US011986478B2

(12) United States Patent
Yuan et al.

(10) Patent No.: US 11,986,478 B2
(45) Date of Patent: May 21, 2024

(54) TARGETING PAPAIN-LIKE PROTEASE FOR BROAD-SPECTRUM CORONAVIRUSES INHIBITION

(71) Applicants: Versitech Limited, Hong Kong (CN); Centre for Virology, Vaccinology and Therapeutics Limited, Hong Kong (CN)

(72) Inventors: Shuofeng Yuan, Hong Kong (CN); Fuk Woo Jasper Chan, Hong Kong (CN); Kwok Yung Yuen, Hong Kong (CN)

(73) Assignees: Versitech Limited, Hong Kong (CN); Centre for Virology, Vaccinology and Therapeutics Limited, Hong Kong (CN)

( * ) Notice: Subject to any disclaimer, the term of this patent is extended or adjusted under 35 U.S.C. 154(b) by 0 days.

(21) Appl. No.: 17/823,559

(22) Filed: Aug. 31, 2022

(65) Prior Publication Data

US 2023/0241067 A1    Aug. 3, 2023

Related U.S. Application Data

(60) Provisional application No. 63/260,771, filed on Aug. 31, 2021.

(51) Int. Cl.
*A61K 31/519*    (2006.01)
*A61K 9/00*    (2006.01)
*A61P 31/14*    (2006.01)
*C12Q 1/6888*    (2018.01)

(52) U.S. Cl.
CPC .......... *A61K 31/519* (2013.01); *A61K 9/0019* (2013.01); *A61K 9/0053* (2013.01); *A61P 31/14* (2018.01); *C12Q 1/6888* (2013.01)

(58) Field of Classification Search
CPC ............................ A61K 31/519; A61P 31/14
See application file for complete search history.

(56) References Cited

U.S. PATENT DOCUMENTS

2020/0222416 A1* 7/2020 Pancholi .............. A61K 31/545

FOREIGN PATENT DOCUMENTS

CN           112043706 A   * 12/2020

OTHER PUBLICATIONS

Hanson et al. "Infectious Diseases Society of American Guidelines on the Diagnosis of coronavirus disease 2019," Clinical Infectious Diseases, 2020, ciaa760, https://doi.org/10.1093/cid/ciaa760. (Year: 2019).*

(Continued)

*Primary Examiner* — San Ming R Hui
(74) *Attorney, Agent, or Firm* — SALIWANCHIK, LLOYD & EISENSCHENK

(57) ABSTRACT

The subject invention pertains to compounds and methods of using said compounds to target the multi-functional papain-like protease (PLpro) domain of the viral Nsp3, specifically F0213, F0326, and F0393 that can have broad anti-coronavirus activity, including SARS-CoV-2, MERS-CoV, and coronaviruses hCoV-229E and hCoV-OC43. F0213, F0326, and F0393 can possess a dual therapeutic functionality that suppress CoV replication via blocking viral polyprotein cleavage, as well as promote antiviral immunity by antagonizing the PLpro deubiquitinase activity.

14 Claims, 28 Drawing Sheets
Specification includes a Sequence Listing.

(56) References Cited

OTHER PUBLICATIONS

PubChem CID 50761577 (Year: 2011).*
CAS registry No. 1111010-58-2 (Year: 2009).*
Fu, Z., et al.,. "The complex structure of GRL0617 and SARS-CoV-2 PLpro reveals a hot spot for antiviral drug discovery," Nature Communications, 2021, 12(488):1-12.
Zhao, Y., et al., "High-throughput screening identifies established drugs as SARS-CoV-2 PLpro inhibitors," Protein Cell, 2021, 12(11):877-888.

* cited by examiner

Compound F0326

Compound F0393

TARGETING PAPAIN-LIKE PROTEASE FOR BROAD-SPECTRUM CORONAVIRUSES INHIBITION

CROSS-REFERENCE TO RELATED APPLICATION

This application claims the benefit of U.S. Provisional Application Ser. No. 63/260,771, filed Aug. 31, 2021, which is hereby incorporated by reference in its entirety including any tables, figures, or drawings.

REFERENCE TO SEQUENCE LISTING

The Sequence Listing for this application is labeled "UHK270XC1.xml" which was created on Aug. 31, 2022 and is 6,206 bytes. The entire content of the sequence listing is incorporated herein by reference in its entirety.

BACKGROUND OF THE INVENTION

The ongoing prevalence of COVID-19 and appearance of variants of concern (VOC) with more rapid transmission capacity, immune evasion has highlighted the general lack of antiviral small molecule drugs to fight a global coronavirus pandemic (https://www.cdc.gov/coronavirus/2019-ncov/variants/variant-info.html). Within the past two decades, another two coronaviruses have emerged to cause epidemics or pandemics in humans: severe acute respiratory syndrome coronavirus (SARS-CoV) in 2002-2003 and Middle East respiratory syndrome coronavirus (MERS-CoV) since 2012. Moreover, circulating common cold human coronaviruses (hCoV) including hCoV-OC43, hCoV-229E, hCoV-NL63, and hCoV-HKU1 contribute notably to morbidity, especially in the elderly and immunocompromised[1]. Therefore, a highly effective antiviral with broad-spectrum coronaviruses coverage would facilitate the control of existing and emerging coronavirus diseases in the future.

Targeting a proteolytic viral papain-like cysteine protease (PLpro) is promising because coronaviruses express their protein machinery as a polyprotein that requires cleavage into functional units. Other PLpro enzymatic activities involve the removal of the cellular substrates ubiquitin (Ub), termed deubiquitination (DUB), and interferon-stimulated gene 15 (ISG15), termed deISGylation, from host cell proteins[2]. As a result, coronaviruses with blocked PLpro protease activity lose their ability to replicate in cells. Strategically, targeting PLpro with antiviral drugs may have an advantage in not only inhibiting viral replication but also inhibiting the dysregulation of signaling cascades in infected cells that may lead to cell death in surrounding, uninfected cells[3]. However, there has been no PLpro-targeting inhibitor with pan-coronaviral coverage published to date.

SARS-CoV-2-PLpro shares 51.1% sequence similarity with that of MERS-CoV. Both SARS-CoV-2 and MERS-CoV belong to Betacoronavirus group 2, encode only one PLpro domain within Nsp3, which is an ortholog to the PLP2 domain from other CoVs encoding two PLpro domains. Although CoV PLpros catalyze the same chemical reaction, i.e., hydrolysis of peptide and isopeptide bonds, these closely related orthologs can differ significantly in terms of substrate recognition, enzymatic activity and inhibition by small-molecule compounds. For example, SARS-CoV-2-PLpro preferentially cleaves ISG15 from substrates over ubiquitin chains; whereas, SARS-CoV-1-PLpro targets ubiquitin chains more than ISG15[4]. SARS-CoV-1-PLpro shows more robust catalytic activity than MERS-CoV-PLpro toward most substrates and exhibits a unique bivalent recognition mechanism toward polyubiquitin substrates. Both enzymes are capable of recognizing and hydrolyzing fluorophores from the C termini of RLRGG peptide, Ub, and ISG15 substrates, yet the kinetic parameters associated with these reactions are different[5].

Therefore, there remains a need for a PLpro-targeting inhibitor with pan-coronaviral coverage.

BRIEF SUMMARY OF THE INVENTION

The subject invention pertains to a novel pan-coronavirus PLpro inhibitors, including, for example F0213, F0326, and F0393 and compounds thereof. In certain embodiments, the pan-coronavirus PLpro inhibitor can be used in methods to treat viral infections; the pan-coronavirus PLpro inhibitor has in vivo antiviral efficacy. In certain embodiments, inhibitors F0213, F0326, and F0393 can have broad coverage of anti-coronavirus activity, including pandemic SARS-CoV-2, epidemic MERS-CoV, as well as seasonal coronaviruses hCoV-229E and hCoV-OC43.

BRIEF DESCRIPTION OF THE DRAWINGS

(FIG. 1A) Results from screening 50,080 compounds in duplicate for inhibition of PLpro activity. The replicate plot shows the percentage inhibition of PLpro by each compound. The structure of the lead compound 7724772 is shown, and its activity is plotted in red. The hit zone for the assay (35% inhibition) is indicated by a white box. (FIG. 1B) In vitro inhibition for SARS2 PLpro of the selected primary hits. (FIG. 1C) In vitro inhibition for MERS-CoV PLpro of the selected primary hits. The ubiquitin-like peptide substrate was used in both (FIG. 1B) and (FIG. 1C) taking GRL0617 as a control. (FIGS. 1D-1F) Dose-response relationships of selected antiviral compounds, depicting infectivity (squares), cytotoxicity (circles), and IC50 values. (FIGS. 1G-1H) Immunofluorescence staining of SARS-CoV-2 NP antigen (Magenta) and MERS-CoV-NP antigen (green), and Vero cell nucleus (blue). Cells (0.1 MOI) were treated by DMSO (0.1%), Remdesivir (10 µM), GRL0617 (20 µM), or F0213 (10 µM) for 24 h, respectively. Shown are representative images selected from a pool images captured in two independent experiments. One-way ANOVA when compared with the DMSO group of wither SARS-CoV-2 or MERS-CoV infection. ****$p<0.0001$ and n.s. indicates $p>0.05$.

(FIG. 2A) Dose-response analysis of F0213 against SARS-CoV-2 variants of concern in VeroE6/TMPRSS2 cells. EC50 was achieved by plaque reduction assays. (FIG. 2B) F0213 inhibited SARS-CoV-2 (0.1 MOI) replication in human primary CMs. Cell lysates were collected for viral load determination. Data represent mean±SD for n=3 biological replicates. (FIG. 2C) Antiviral activity of F0213 against MERS-CoV (0.01 MOI, 48 hpi), HCoV-229E (0.001 MOI, 72 hpi), and HCoV-OC43 (0.001 MOI, 72 hpi) in cell lines as indicated. Viral load in the cell lysate was quantified by RT-qPCR assays. Data represent mean±SD for n=3 biological replicates. One-way ANOVA for statistical analysis were compared with the DMSO group (0 µM), **$p<0.0001$, *$p<0.001$, **$p<0.01$ and *$p<0.05$.

(FIG. 3C) Specificity of F0213 for PLpro over human DUBs. Left panel: An anti-HA Western blot of lysed human colon Caco2 cells treated with HA-Ub-VS in the presence of N-ethyl-maleimide (NEM, positive control inhibitor) or GRL0617 (negative control). Right panel: 0.1p g of SARS-CoV-2 PLpro was added to Caco2 cell lysate before covalent modification by HA-Ub-VS. GRL0617 was taken as a positive control inhibitor that eliminated PLpro-based modification. F0213 antagonized PLpro suppression on IFN-β (FIG. 3D), NF-κB (FIG. 3E), or IRF3 (FIG. 3F) expression. Dual-luciferase reporter gene assays were performed in HEK293T cells. Cells were transfected with indicated SARS-CoV-2-PLpro or MERS-CoV-PLpro and treated with either poly(I:C) to induce reporter gene expression, respectively. All data are presented as mean±s.d. One-way AVONA for statistical analysis were compared with the DMSO group (0 μM). For all statistical analysis, **p<0.0001, *p<0.001, **p<0.01, *p<0.05 and n.s. non-significant.

(FIG. 4A) Docking F0213 to SARS-CoV-2 PLpro: molecular surface of SARS-CoV-2 PLpro (colored cyan) with GRL0617 (colored gold, PDB: 7 JRN) and F0213 (colored magenta, docking model) shown in stick model. The substrate binding cleft and the BL2 loop near active site is indicated. (FIG. 4B) Ribbon model of SARS-CoV-2 PLpro with bound mouse ISG15 (colored yellow, PDB: 6 YVA). The C-terminus of mISG15 is shown with the stick model. The predicted binding mode of F0213 (magenta) is shown with stick model. (FIG. 4C) Detailed interaction between F0213 and SARS-CoV-2 PLpro; residues were predicted to interact with the inhibitor are shown with the stick models (blue). (FIG. 4D and FIG. 4F) In vitro inhibition of WT and mutant SARS2-PLpro as well as WT and mutant MERS-PLpro by F0213. Fixed concentration of PLpro (0.1 μM) as indicated and 5 μM of RLRGG-AMC substrate were incubated with serial-diluted F0213. Two-way ANOVA when compared with the WT % inhibition of in each F0213 concentration. **p<0.0001, *p<0.001, **p<0.01, *p<0.05. (FIG. 4E) Docking F0213 to MERS-CoV PLpro. Left, ribbon model of MERS-CoV PLpro (colored light blue) bound by human ISG15 (colored yellow, PDB: 6BI8) is overlaid with the predicted binding mode of F0213 (colored magenta, docking model). The BL2 loop is indicated. Right, detailed interaction between F0213 and MERS-CoV PLpro; residues that were predicted to interact with the inhibitor are shown with the stick models and colored blue.

(FIG. 5A) Therapeutic treatment used oral (PO) or intraperitoneal (IP) administration of F0213 (5 mg/kg/day), given at 6 hpi, 24 hpi and 48 hpi after virus challenge at day 0. Lung tissue samples were collected at 4 dpi. Remdesivir (20 mg/kg/day) was included as a control via IP route. Vehicle contains 2% DMSO in 12% SBE-β-CD and by IP injection. Viral yields in hamster lungs were determined by plaque assay (FIG. 5B) and RT-qPCR assay (FIG. 5C), respectively. (FIG. 5D) Representative image of infected cells by immunofluorescence staining in lung. SARS-CoV-2 N expression (green) is shown in diffuse alveolar areas. N-positive cells per 50× field per hamster lung section. (FIG. 5E) Representative images of H & E-stained lung tissue section from hamsters treated as indicated, followed by semi-quantitation of histology scores given to each lung tissue by grading the severity of damage in bronchioles, alveoli and blood vessels and accumulating the total scores. Scale bars, 200 μm. One-way ANOVA followed by Dunnett's post test and compared with vehicle control. **P<0.0001, *p<0.001.

(FIG. 6A) Therapeutic treatment used intraperitoneal (IP) administration of F0213 (20 mg/kg/day), given at 6 hpi, 24 hpi and 48 hpi after virus challenge at day 0. Lung tissue samples were collected at 4 dpi. Remdesivir (20 mg/kg/day) was included as a control via IP route. Vehicle contains 2% DMSO in 12% SBE-β-CD and by IP injection. (FIG. 6B) Survival and clinical disease were monitored for 14 days or until death. *P<0.05 by log-rank (Mantel-Cox) tests. (FIG. 6C) Daily body weights of surviving mice. (FIGS. 6D-6E) Lung tissues were collected for detection of viral titers at 3 dpi. A value of 30 PFU/ml was assigned for any titer below the 50 PFU/ml detection limit (the dotted line). One-way ANOVA when compared with the vehicle group. *p<0.05 and **p<0.01.

(FIG. 7D) The cell viability was determined using CellTiter-Glo assays and in the absence of virus infection. The drug-incubation time in the cytotoxicity assay was consistent with that in the antiviral assays as shown in FIGS. 2A-2C e.g. at 24 h post-treatment for Huh7 cells; at 48 h post-treatment for VeroE6/TMPRSS2 cells, Calu-3 and Caco-2 cells; and at 72 h post-treatment for BSC1 cells and human embryonic lung fibroblasts (HELF), respectively. Data represent mean SD for n=3 biological replicates. The experiment was repeated twice for confirmation.

(FIG. 8A) Determination of the cellular protease activity in the presence of F0213 (100, 20, 4 and 0 μM). Lysates of human liver Huh-7 cells, human colon Caco-2 cells and human lung A549 cells were incubated with a fluorescent-casein substrate before reading, detecting a wide variety of proteases including serine proteases (trypsin, chymotrypsin, thrombin, plasmin, elastase, subtilisin), cysteine proteases (papain, cathepsin B) and acid proteases (thermolysin, pepsin). (FIGS. 8B-8E) mRNA expression of IFN-responsive and proinflammatory host genes in the presence of virus infection and F0213 treatment. RT-qPCR analysis was performed utilizing the cell lysate RNA extraction of Caco-2 (SARS-CoV-2, 0.1 MOI, 24 hpi) or Huh-7 (MERS-CoV, 0.1 MOI, 24 hpi), with or without 10 μM F0213 treatment. Data was shown as mean±SD (gene copy per 1000 β-actin). Student's T-test.

BRIEF DESCRIPTION OF THE SEQUENCES

Figure 1A:
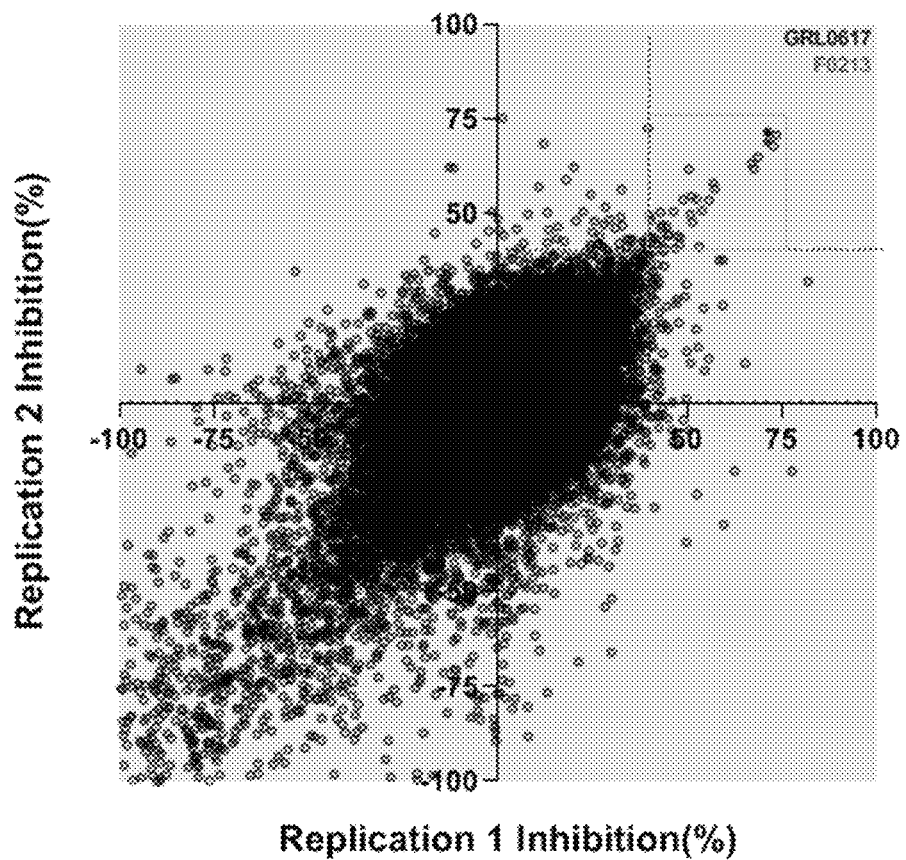
FIGS. 1A-1H. High-throughput screening using a peptide substrate identifies a PLpro inhibitor.

SEQ ID NO: 1 HCoV-229E_Forward DNA Primer
SEQ ID NO: 2 HCoV-229E_Reverse DNA Primer
SEQ ID NO: 3 HCoV-OC43_Forward DNA Primer
SEQ ID NO: 4: HCoV-OC43_Reverse DNA Primer
SEQ ID NO: 5: HCoV-NL63_Forward DNA Primer
SEQ ID NO: 6: HCoV-NL63_Reverse DNA Primer

DETAILED DISCLOSURE OF THE INVENTION

Selected Definitions

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which depends in part on how the value is measured, i.e., the limitations of the measurement system. In the context of compositions containing amounts of ingredients where the terms "about" is used, these compositions contain the stated amount of the ingredient with a variation (error range) of 0-10% around the value (X±10%). In other contexts the term "about" is provides a variation (error range) of 0-10% around a given value (X±10%). As is apparent, this variation represents a range that is up to 10% above or below a given value, for example, X±1%, X±2%, X±3%, X±4%, X±5%, X±6%, X 7%, X±8%, X±9%, or X±10%.

In the present disclosure, ranges are stated in shorthand to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, combinations and subcombinations of ranges (e.g., subranges within the disclosed range) and specific embodiments therein are explicitly included.

As used herein, the term "subject" refers to an animal, needing or desiring delivery of the benefits provided by a drug. The animal may be for example, humans, pigs, horses, goats, cats, mice, rats, dogs, apes, fish, chimpanzees, orangutans, guinea pigs, hamsters, cows, sheep, birds, chickens, as well as any other vertebrate or invertebrate. These benefits can include, but are not limited to, the treatment of a health condition, disease or disorder; prevention of a health condition, disease or disorder; immune health; enhancement of the function of an organ, tissue, or system in the body. The preferred subject in the context of this invention is a human. The subject can be of any age or stage of development, including infant, toddler, adolescent, teenager, adult, or senior.

As used herein, the terms "therapeutically-effective amount," "therapeutically-effective dose," "effective amount," and "effective dose" are used to refer to an amount or dose of a compound or composition that, when administered to a subject, is capable of treating, preventing, or improving a condition, disease, or disorder in a subject. In other words, when administered to a subject, the amount is "therapeutically effective." The actual amount will vary depending on a number of factors including, but not limited to, the particular condition, disease, or disorder being treated, prevented, or improved; the severity of the condition; the weight, height, age, and health of the patient; and the route of administration.

As used herein, the term "treatment" refers to eradicating, reducing, ameliorating, or reversing a sign or symptom of a health condition, disease or disorder to any extent, and includes, but does not require, a complete cure of the condition, disease, or disorder. Treating can be curing, improving, or partially ameliorating a disorder. "Treatment" can also include improving or enhancing a condition or characteristic, for example, bringing the function of a particular system in the body to a heightened state of health or homeostasis.

As used herein, "preventing" a health condition, disease, or disorder refers to avoiding, delaying, forestalling, or minimizing the onset of a particular sign or symptom of the condition, disease, or disorder. Prevention can, but is not required, to be absolute or complete; meaning, the sign or symptom may still develop at a later time. Prevention can include reducing the severity of the onset of such a condition, disease, or disorder, and/or inhibiting the progression of the condition, disease, or disorder to a more severe condition, disease, or disorder.

In some embodiments of the invention, the method comprises administration of multiple doses of the compounds of the subject invention. The method may comprise administration of 1, 2, 3, 4, 5, 6, 7, 8, 9, 10, 15, 20, 25, 30, 35, 40, or more therapeutically effective doses of a composition comprising the compounds of the subject invention as described herein. In some embodiments, doses are administered over the course of 1 day, 2 days, 3 days, 4 days, 5 days, 6 days, 7 days, 10 days, 14 days, 21 days, 30 days, or more than 30 days. The frequency and duration of administration of multiple doses of the compositions is such as prevent or treat a viral infection. Moreover, treatment of a subject with a therapeutically effective amount of the compounds of the invention can include a single treatment or can include a series of treatments. It will also be appreciated that the effective dosage of a compound used for treatment may increase or decrease over the course of a particular treatment. Changes in dosage may result and become apparent from the results of testing for a virus. In some embodiments of the invention, the method comprises administration of the compounds at several time per day, including but not limiting to 2 times per day, 3 times per day, and 4 times per day.

As used herein, an "isolated" or "purified" compound is substantially free of other compounds. In certain embodiments, purified compounds are at least 60% by weight (dry weight) of the compound of interest. Preferably, the preparation is at least 75%, more preferably at least 90%, and most preferably at least 99%, by weight of the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

By "reduces" is meant a negative alteration of at least 1%, 5%, 10%, 25%, 50%, 75%, or 100%.

By "increases" is meant as a positive alteration of at least 1%, 5%, 10%, 25%, 50%, 75%, or 100%.

As used herein, a "pharmaceutical" refers to a compound manufactured for use as a medicinal and/or therapeutic drug.

PLpro

The subject invention pertains to a method for treatment or prevention of a coronavirus infection, such as SARS-CoV-2, in a subject, comprising administering to the subject an effective amount compounds that can target at least one of the three distinct substrates of PLpro, namely the viral polyprotein, degradative Lys48-polyubiquitin and antiviral ISG15 signals or a pharmaceutically acceptable salt, derivative, or prodrug thereof.

The PLpro inhibitor may be administered to the human subject before or after initiation of the coronavirus infection, thereby treating the coronavirus infection. In some embodiments, the subject has the disease COVID-19 at the time that one or more PLpro inhibitor(s) is/are administered.

In certain embodiments, the PLpro inhibitor can be administered after the viral infection. The PLpro inhibitor can limit or prevent complications or symptoms of the previous infection.

Another aspect of the invention concerns a method for inhibiting a human coronavirus infection in a human cell, comprising contacting a viral particle cell with a PLpro inhibitor, or a pharmaceutically acceptable salt, derivative, or prodrug thereof, before or after the viral particle infects a cell.

The human coronavirus may be any time or subgroup, including alpha, beta, gamma, and delta. In some embodiments of the aforementioned methods of the invention, the human coronavirus is selected from among SARS-CoV-2, SARS-CoV, and MERS-CoV. In some embodiments of the aforementioned methods of the invention, the human coronavirus is a common human coronavirus, such as type 229E, NL63, OC43, and HKU1.

Another aspect of the invention concerns a composition comprising a PLpro inhibitor, or a pharmaceutically acceptable salt, derivative, or prodrug thereof.

In one embodiment of the compositions and methods of the invention, the PLpro inhibitor comprises one or more compounds disclosed herein including, for example, formula (I) (F0213), formula (II) (F0326), or formula (III) (F0393), or a structural or functional derivative thereof that retains PLpro inhibitory activity, or a pharmaceutically acceptable salt of any of the foregoing.

formula (I)

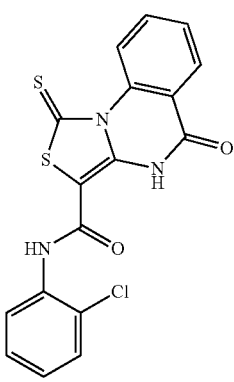

formula (II)

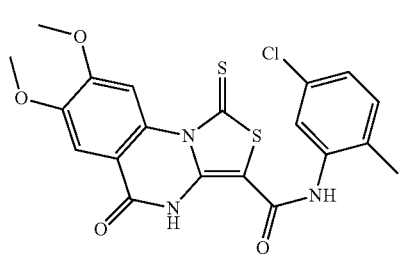

formula (III)

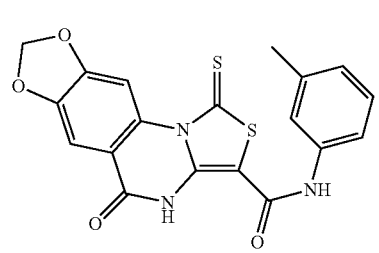

Compositions and Treatment

The PLpro inhibitors of the present invention can be formulated into pharmaceutically acceptable salt forms or hydrate forms. Pharmaceutically acceptable salt forms include the acid addition salts and include hydrochloric, hydrobromic, nitric, phosphoric, carbonic, sulfuric, and organic acids like acetic, propionic, benzoic, succinic, fumaric, mandelic, oxalic, citric, tartaric, maleic, and the like. Pharmaceutically acceptable base addition salts include sodium, potassium, calcium, ammonium, and magnesium salts. Pharmaceutically acceptable salts of the polypeptides of the invention can be prepared using conventional techniques.

Administration of one or more PLpro inhibitors can be carried out in the form of an oral tablet, capsule, or liquid formulation containing a therapeutically effective amount of the active ingredient (PLpro inhibitor). Administration is not limited to oral delivery and includes intravascular (e.g., intravenous), intramuscular, or another means known in the pharmaceutical art for administration of active pharmaceutical ingredients.

Therapeutic or prophylactic application of the PLpro inhibitors and compositions containing thereof, can be accomplished by any suitable therapeutic or prophylactic method and technique presently or prospectively known to those skilled in the art. The PLpro inhibitors can be administered by any suitable route known in the art including, for example, oral, intramuscular, intraspinal, intracranial, nasal, rectal, parenteral, subcutaneous, or intravascular (e.g., intravenous) routes of administration. Administration of the PLpro inhibitors of the invention can be continuous or at distinct intervals as can be readily determined by a person skilled in the art.

In some embodiments, an amount of PLpro inhibitors can be administered 1, 2, 3, 4, or times per day, for 1, 2, 3, 4, 5, 6, 7, or more days. Treatment can continue as needed, e.g., for several weeks. Optionally, the treatment regimen can include a loading dose, with one or more daily maintenance doses. For example, in some embodiments, an initial loading dose in the range of 100 mg to 1,000 is administered, followed by a maintenance dose in the range of 100 mg to 1,000 mg every 12 hours for 1, 2, 3, 4, 5, 6, 7, or more days.

In some embodiments, an initial loading dose in the range of 200 mg to 600 mg is administered, followed by a maintenance dose in the range of 100 mg to 300 mg every 12 hours for 1, 2, 3, 4, 5, 6, 7, or more days.

PLpro inhibitors and compositions comprising said inhibitors can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive inhibitor is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject inhibitors include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the inhibitors can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the inhibitor based on the weight of the total composition including carrier or diluent.

The PLpro inhibitors can also be administered utilizing liposome technology, slow-release capsules, implantable pumps, and biodegradable containers. These delivery methods can, advantageously, provide a uniform dosage over an extended period of time.

The subject invention also concerns a packaged dosage formulation comprising in one or more packages, packets, or containers at least one PLpro inhibitor and/or composition of the subject invention formulated in a pharmaceutically acceptable dosage. The package can contain discrete quantities of the dosage formulation, such as tablet, capsules, lozenge, and powders. The quantity of PLpro inhibitor in a dosage formulation and that can be administered to a patient can vary from about 1 mg to about 5000 mg, or about 1 mg to about 2000 mg, or more typically about 1 mg to about 500 mg, or about 5 mg to about 250 mg, or about 10 mg to about 100 mg. In some embodiments, the amount is in the range of 100 mg to 600 mg, to be administered 1, 2, 3, or 4 times per day, for 2, 3, 4, 5, 6, 7 or more days.

The subject invention also concerns kits comprising in one or more containers a PLpro inhibitor. A kit of the invention can also comprise one or more compounds, biological molecules, or drugs. In one embodiment, a kit of the invention comprises a PLpro inhibitor.

Optionally, the methods further comprise, prior to administering the PLpro inhibitor to the subject, identifying the subject as having a human coronavirus infection (human coronavirus, generally, or a specific strain of coronavirus, such as SARS-CoV-2), or not having a human coronavirus infection. If the subject is identified as having a human coronavirus infection, the PLpro inhibitor can be administered to the human subject as therapy. If the human subject is identified as not having a human coronavirus infection, the PLpro inhibitor can be withheld, or the PLpro inhibitor can be administered as prophylaxis, or an alternative agent can be given. The identifying step may comprise assaying a biological sample (e.g., blood, saliva, or urine) obtained from the subject for the presence of human coronavirus nucleic acids or human coronavirus proteins, such as SARS-CoV-2 nucleic acids or proteins. In some embodiments, assaying includes the use of reverse transcriptase-polymerase chain reaction (RT-PCR), immunological assay (e.g., ELISA), or Plaque-reduction neutralization testing (PRNT).

Thus, optionally, the methods include, prior to administration of the PLpro inhibitor, or re-administration of the PLpro inhibitor, determining whether the subject has a human coronavirus infection or one or more symptoms consistent with a human coronavirus infection. Some individuals infected with coronavirus will not know they have the infection because they will not have symptoms.

In some embodiments of the methods of the invention, the human coronavirus is selected from among SARS-CoV-2, SARS-CoV, and MERS-CoV. SARS-CoV-2 is a novel human coronavirus that causes coronavirus disease 2019, also known as COVID-19 and COVID19. MERS-CoV is the beta coronavirus that causes Middle East Respiratory Syndrome, or MERS. SARS-CoV is the beta coronavirus that causes severe acute respiratory syndrome, or SARS.

In some embodiments of the methods of the invention, the human coronavirus is a common human coronavirus, such as type 229E (an alpha coronavirus), NL63 (an alpha coronavirus), OC43 (a beta coronavirus), and HKU1 (a beta coronavirus).

The symptoms of a coronavirus infection depend on the type of coronavirus and severity of the infection. If a subject has a mild to moderate upper-respiratory infection, such as the common cold, symptoms may include runny nose, headache, cough, sore throat, fever, and general feeling of being unwell. Some coronaviruses can cause severe symptoms. These infections may turn into bronchitis and pneumonia, which can cause symptoms such as fever (which can be quite high with pneumonia), cough with mucus, shortness of breath, and chest pain or tightness when the subject breaths or coughs.

The clinical spectrum of SARS-CoV-2 may range from mild disease with non-specific signs and symptoms of acute respiratory illness, to severe pneumonia with respiratory failure and septic shock. Asymptomatic infections have also been reported.

To diagnose coronavirus infections, healthcare providers typically take the subject's medical history and ask the subject their symptoms, do a physical examination, and may conduct laboratory tests on a biological sample such as blood, or a respiratory specimen such as sputum or a throat swab.

SARS-CoV-2 RNA has been detected from upper and lower respiratory tract specimens, and the virus has been isolated from upper respiratory tract specimens and bronchoalveolar lavage fluid. SARS-CoV-2 RNA has been detected in blood and stool specimens. The duration of SARS-CoV-2 RNA detection in the upper and lower respiratory tracts and in extrapulmonary specimens has not been determined. It is possible that RNA could be detected for weeks, which has occurred in some cases of MERS-CoV or SARS-CoV infection. Viable SARS-CoV has been isolated from respiratory, blood, urine, and stool specimens, and viable MERS-CoV has been isolated from respiratory tract specimens.

Treatment methods optionally include steps of advising that the subject get plenty of rest and drink fluids for hydration and administration of agents that alleviate symptoms of coronavirus infection, such as those that reduce fever and pain (e.g., acetaminophen and/or paracetamol), particularly for common human coronavirus infections. The methods may include administration of the fluids to the subject for hydration.

The subject may be any age or gender. In some cases, the subject may be an infant or older adult. In some embodiments, the subject is 40 years of age or older. In some embodiments, the subject is 55 years of age or older. In some embodiments, the subject is 60 years of age or older. In some embodiments, the subject is an infant. In some embodiments, the subject (of any age or gender) has heart or lung disease, diabetes, or a weakened immune system.

The invention further provides kits, including PLpro inhibitors and pharmaceutical formulations, packaged into suitable packaging material, optionally in combination with instructions for using the kit components, e.g., instructions for performing a method of the invention. In one embodiment, a kit includes an amount of a PLpro inhibitor and instructions for administering the inhibitor to a subject in need of treatment on a label or packaging insert. In further embodiments, a kit includes an article of manufacture, for delivering the inhibitor into a subject locally, regionally or systemically, for example.

As used herein, the term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention, e.g., treating a human coronavirus infection, an assay for identifying a subject having a human coronavirus infection, etc. Thus, in additional embodiments, a kit includes a label or packaging insert including instructions for practicing a method of the invention in solution, in vitro, in vivo, or ex vivo.

Instructions can therefore include instructions for practicing any of the methods of the invention described herein. For example, pharmaceutical compositions can be included in a container, pack, or dispenser together with instructions for administration to a subject to treat a human coronavirus infection. Instructions may additionally include appropriate administration route, dosage information, indications of a satisfactory clinical endpoint or any adverse symptoms that may occur, storage information, expiration date, or any information required by regulatory agencies such as the Food and Drug Administration or European Medicines Agency for use in a human subject.

The instructions may be on "printed matter," e.g., on paper or cardboard within the kit, on a label affixed to the kit or packaging material, or attached to a vial or tube containing a component of the kit. Instructions may comprise voice or video tape and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Kits can additionally include a buffering agent, a preservative, or an agent for stabilizing the PLpro inhibitor. The kit can also include control components for assaying for the presence of human coronavirus, e.g., a control sample or a standard. Each component of the kit can be enclosed within an individual container or in a mixture and all of the various containers can be within single or multiple packages.

In certain embodiments, the coronaviral PLpro can have broad-spectrum pharmacological intervention. Compared with GRL0617, a 'model' compound that have been extensively analyzed in our and others' studies on SARS-CoV or SARS-CoV-2-PLpro[15-17], F0213, F0326, and F0393 represent a new generation of compounds to facilitate the design of pan-coronaviral PLpro inhibitors.

F0213, F0326, and F0393 can be the first PLpro inhibitors that are orally available, which offer a potential at-home treatment for reducing the burdens of healthcare facilities.

MATERIALS AND METHODS

Viruses and Cells

SARS-CoV and SARS-CoV-2 (lineage B βCoV), MERS-CoV (lineage C βCoV), HCoV-OC43 (lineage A βCoV), and HCoV-229E (αCoV) were included in this study to represent the subgroups of CoVs that cause human infections. The SARS-CoV-2 HKU-001a strain (GenBank accession number: MT230904) was isolated from the nasopharyngeal aspirate specimen of a patient who was laboratory-confirmed to have COVID-19 in Hong Kong[18]. MERS-CoV (EMC/2012) was kindly provided by Ron Fouchier (Erasmus Medical Center, the Netherlands). Archived clinical strains of SARS-CoV, HCoV-OC43, and HCoV-229E were obtained from the Department of Microbiology, The University of Hong Kong (HKU). All the cell lines used in this study, except for HEL (human embryonic lung fibroblasts; in-house development), were obtained from American Type Culture Collection. Experientially, the inhibitory activity of F0213 against 229E replication was tested in HEL cells and OC43 in BSC-1 cells, as we previously described[18].

Viral Load Reduction Assay

Viral load reduction assay was performed by quantitative reverse transcription-polymerase chain reaction (qRT-PCR) as we described previously with slight modifications[19]. Briefly, RNA was extracted from culture supernatants of the CoV-infected cell lines as mentioned above using the MiniBEST Viral RNA/DNA Extraction Kit (Takara Bio Inc., Kusatsu, Shiga Prefecture, Japan). Reverse transcription was performed with the Transcriptor First Strand cDNA Synthesis Kit (Roche, Basel, Switzerland) with oligo-dT primers. To determine the virus genome copies, qPCR was performed using the LightCycler 480 SYBR Green I Master Mix (Roche) with specific primers.

```
HCoV-229E_Forward:
                              (SEQ ID NO: 1)
CTACAGATAGAAAAGTTGCTTT;

HCoV-229E_Reverse:
                              (SEQ ID NO: 2)
GGTCGTTTAGTTGAGAAAAGT;

HCoV-OC43_Forward:
                              (SEQ ID NO: 3)
AAACGTGCGTGCATC;

HCoV-OC43_Reverse:
                              (SEQ ID NO: 4)
AGATTACAAAAAGATCTAACAAGA ;
```

-continued

```
HCoV-NL63_Forward:
                                    (SEQ ID NO: 5)
GGAGATAGAGAATTTTCTTATTTAGA;

HCoV-NL63_Reverse:
                                    (SEQ ID NO: 6)
GGTTTCGTTTAGTTGAGAAG.
```

The virus genome copies in supernatant samples were quantified with a standard.

Plaque Reduction Assay

Plaque reduction assay was performed in 24-well tissue culture plates as we described previously with slight modifications[20]. Briefly, the cells were seeded at $1 \times 10^5$ cells/well in MEM (Invitrogen, Carlsbad, CA, USA) with 10% FBS on the day before the assay was carried out. After 16-24 h of incubation, 70-100 plaque-forming units (PFU) of SARS-CoV-2 or MERS-CoV was added to the cell monolayer with or without the addition of drug compounds and the plates further incubated for 2 h at 37° C. in 5% $CO_2$ before removal of unbound viral particles by aspiration of the media and washing once with MEM. The cell monolayers were then overlaid with media containing 1% low melting agarose (Cambrex, East Rutherford, NJ, USA) in MEM and appropriate concentrations of drug compounds and incubated as above for 72 h. Next, the wells were fixed with 10% formaldehyde overnight. After removal of the agarose plugs, the cell monolayers were stained with 0.7% crystal violet and the plaques counted. The percentage of plaque inhibition relative to the control (without F0213) plates was determined for each drug compound concentration Molecular Docking The crystal structure of SARS-CoV-2 papain-like (PL) protease was downloaded from the Protein Data Bank (PDB code: 7 JRN) (Worldwide website: resb.org/structure/7 JRN)[21]. Protonation states of side chains were predicted using PROPKA3.1 server[22]. The structure of F083-0213 was prepared with OpenBabel 2.3.1, including 3D conformer search, bond order assignment, hydrogen addition and partial charge calculation[23]. Molecular docking was performed by using Autodock Vina with default parameters[24]. The key residues surrounding F083-0213 were visualized with PyMol.

Protease Cleavage Assay

To explore the cleavage inhibition of PLpro against ISG15 and ubiquitin, ubiquitin-AMC or ISG15-AMC were used as substrate of PLpro and the release of AMC was measured by increase of fluorescence (excitation/emission, 360/487 nm) on a 384-well microplate reader (PHERAstar FSX, BMG Labtech, Ortenberg, Germany). 25 microliters of solution containing different concentrations of F0213 (final concentrations range from 100 to 0 µM) and 1 µM of ubiquitin-AMC or ISG15-AMC was aliquoted into a 384 well plate with the reaction initiated by addition of 25 µl of PLpro (0.1 µM) to the well. Initial velocities of AMC release was normalized against DMSO control. The $IC_{50}$ value was calculated by the dose-response-inhibition function in Graphpad Prism with [inhibitor] vs normalized response equation. GRL-0617 was used as a positive control throughout the experiments.

Reporter Gene Assay

To analyze the induction of IFN-0 induced genes in the presence/absence of PLpro, and with or without F0213 treatment, luciferase reporter assays were performed in 293T cells[25]. In brief, an expression construct containing the luciferase ORF and the IFN-β promoter (IFN-β-luciferase) or NF-kb or IRF3 was co-transfected with either a pCAGEN control plasmid or the designated PLpro plasmid and Renilla plasmid. For all transfections, 100 ng of luciferase plasmid, 400 ng of PLpro or pCAGEN vector and 5 ng Renilla plasmid were used in each well of a 24-well plate. Twenty-four hours after transfection, cells were treated with 500 ng poly(I:C) for 18 h or 50 ng/ml of TNF for 30 min. For the F0213 treatment group, serial diluted concentrations of F0213 was added to relative wells after 6 hours poly(I:C) or 50 ng/mL TNF treatment. Luciferase expression was measured using the Luciferase Reporter Assay System (Promega). Fold change was calculated by taking vector treated with poly(I:C) or TNF as 1.

Hamster Experiment

Male and female Syrian hamster, aged 6-10 weeks old, were kept in biosafety level 3 housing and given access to standard pellet feed and water, as we previously established[13]. All experimental protocols were approved by the Animal Ethics Committee in the HKU (CULATR) and were performed according to the standard operating procedures of the biosafety level 3 animal facilities (reference code: CULATR 5370-20). Experimentally, each hamster was intranasally inoculated with $10^5$ PFU of SARS-CoV-2 in 100 µL PBS under intraperitoneal ketamine (200 mg/kg) and xylazine (10 mg/kg) anesthesia. Six-hours post-virus-challenge, hamsters were intraperitoneally given either F0213 (5 mg/kg/day), or Remdesivir (20 mg/kg/day) or PBS (vehicle controls) for consecutive 4 days. Animals were monitored twice daily for clinical signs of disease. Six animals in each group were sacrificed at 4 dpi for virological and histopathological analyses. Viral yield in the lung tissue homogenates was detected by plaque assay and qRT-PCR method, respectively.

hDPP4-KI Mouse Experiment

The hDPP4 exon 10-12 knock-in mice were provided by Dr. Paul McCray (University of Iowa, IA, USA)[14]. Littermates of the same sex were randomly assigned to experimental groups. On the day of infection, the mice were intranasally inoculated with 2000 PFU mouse-adapted MERS-CoV (MERS-CoV$_{MA}$) as we previously described[26]. Infected mice received same regimen as that of hamster experiment except the increasing dose of F0213 (20 mg/kg/day).

Isothermal Titration Calorimeters

The binding affinity between SARS-CoV-2 PLpro and F083-0213 was measured under 25 degrees through isothermal titration calorimeter (MicroCal iTC200, Malvern Panalytical, Malvern, UK). The buffer was 20 mM Tris-HCl PH8.0, 200 mM NaCl, 2 mM DTT and 30% DMSO. The protein concentration in syringe ranged from 0.3 to 0.6 mM while in reaction cell ranged from 0.03 to 0.06 mM. After excluding the first injection, all titration data was calculated and analyzed by MicroCal ITC-ORIGIN Analysis Software (Malvern Panalytical).

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Identification of PLPRO Inhibitors by High-Throughput Screening

Figure 1B:
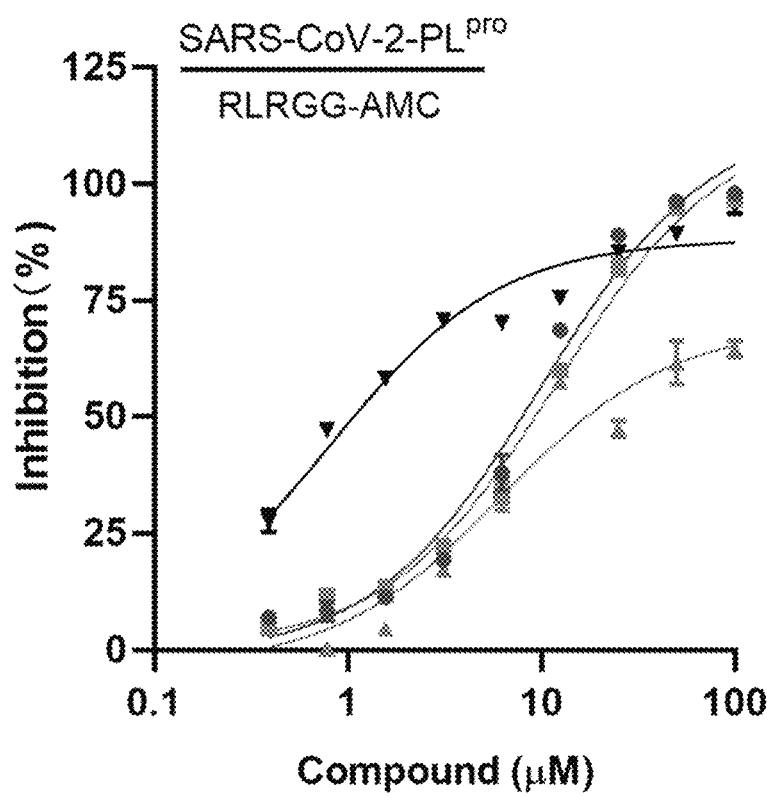
Figure 1C:
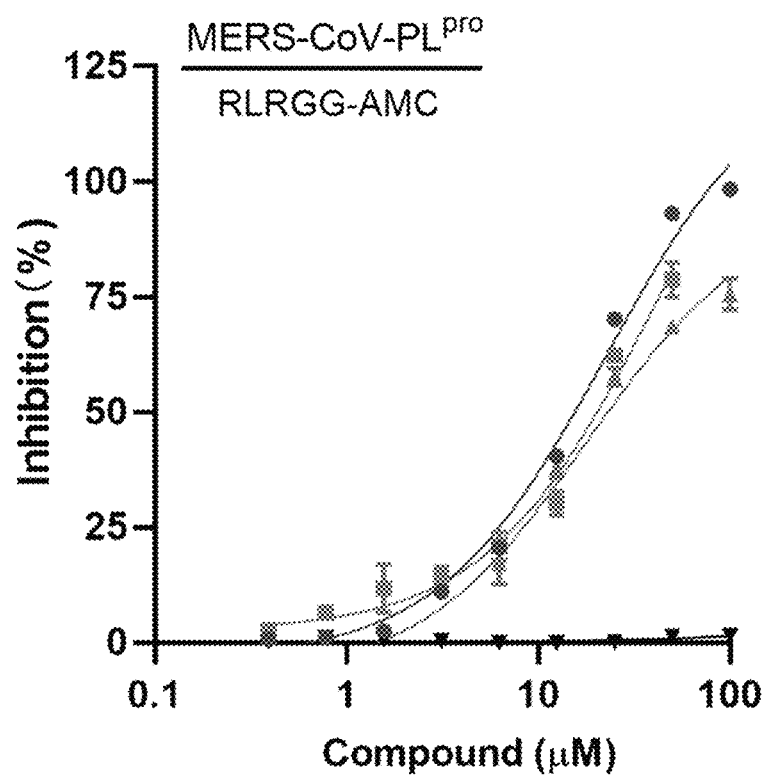

To identify potential PLpro inhibitors, a fluorescence-based high-throughput screen targeting SARS-CoV-2 PLpro cleavage activity was performed[6]. In the interest of developing noncovalent inhibitors, DTT (5 mM) was incorporated into all assays. A primary screen of 50,080 diverse and drug-like compounds was performed in 384-well plates. Only a small number of compounds, i.e. 54 (0.1%), were found to have more than 40% inhibitory activity toward PLpro (FIG. 1A). These primary hits were subjected to a series of confirmatory and secondary assays to exclude the interference from AMC fluorescence, followed by dose-dependent validations against both SARS-CoV-2-PLpro and MERS-CoV-2-PLpro that shares 32.9% amino acid identity. A class of 5-oxo-1-thioxo-4,5-dihydro[1,3]thiazolo[3,4-a] quinazoline-3-carboxamide molecules, designated F0213, F0326 and F0393, exhibited an $IC_{50}$ of 7.4 µM, 8.2 µM and 15.8 µM against SARS-CoV-2-PLpro, respectively (FIG. 1B). As expected, GRL0617 potently inhibited SARS-CoV-2-PLpro ($IC_{50}$=1.1 µM) without impairing the MERS-CoV-PLpro activity (FIG. 1C). In contrast, the 3 hit compounds suppressed MERS-CoV-PLpro with $IC_{50}$s ranging from 10~20 µM.

Figure 1D:
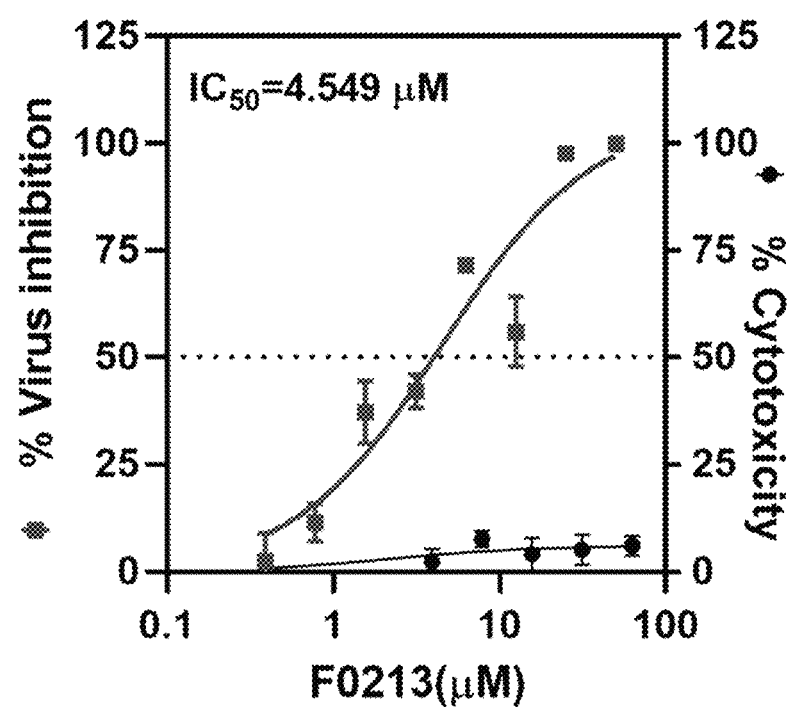
Figure 1E:
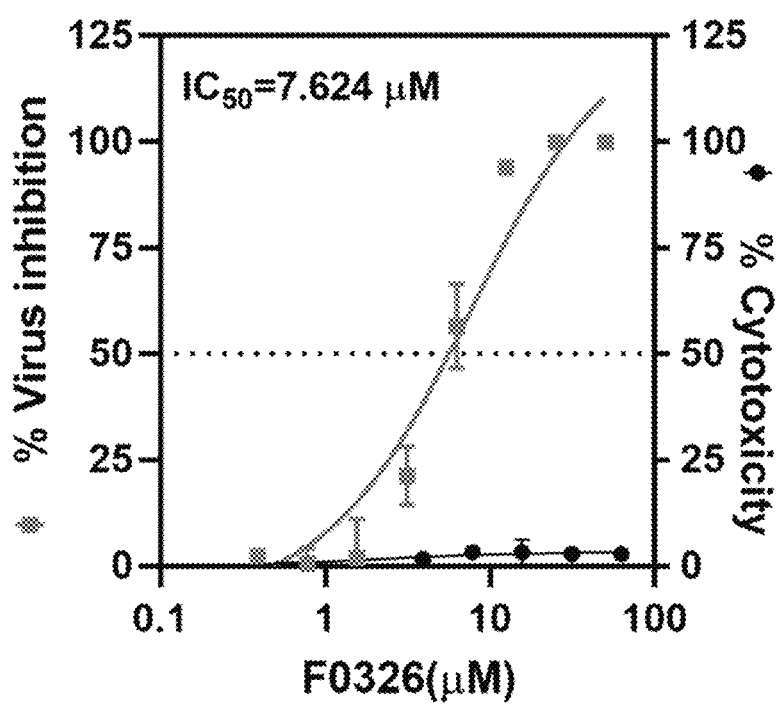
Figure 1F:
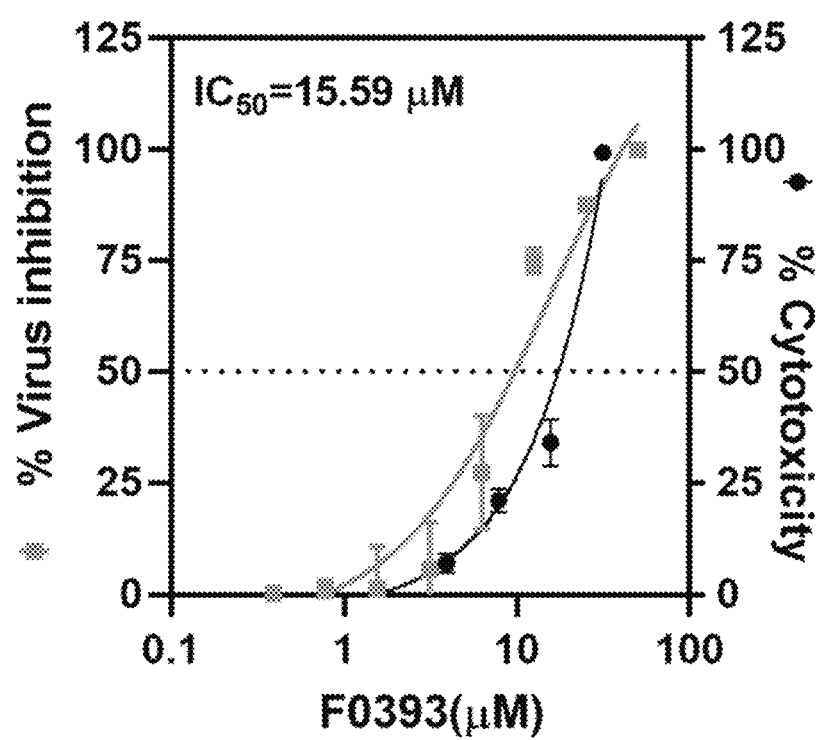
Figure 1G:
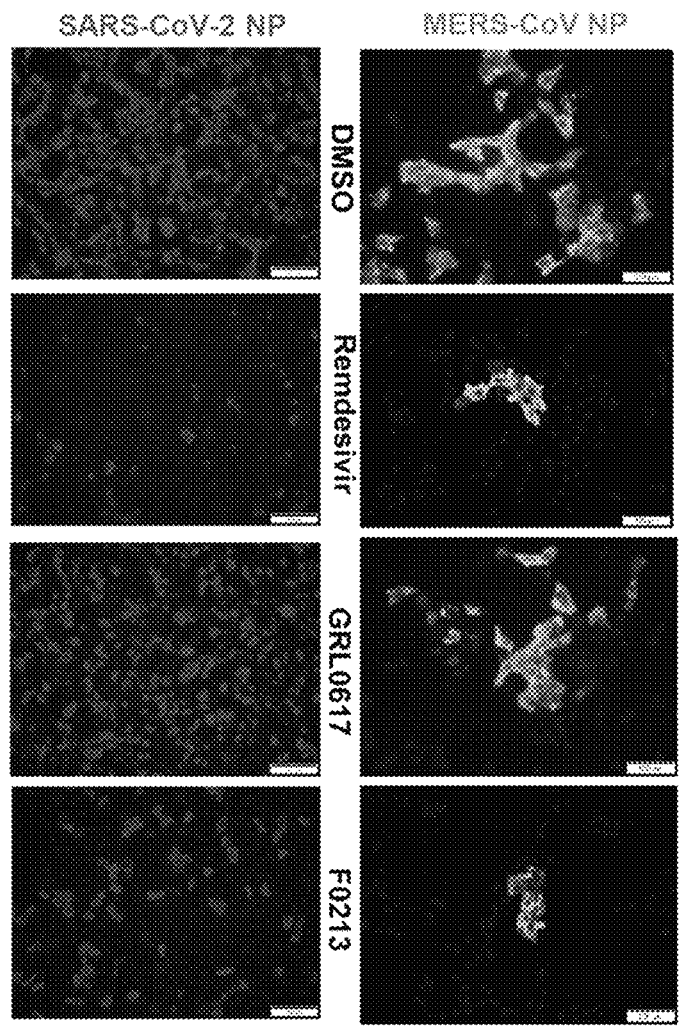
Figure 1H:
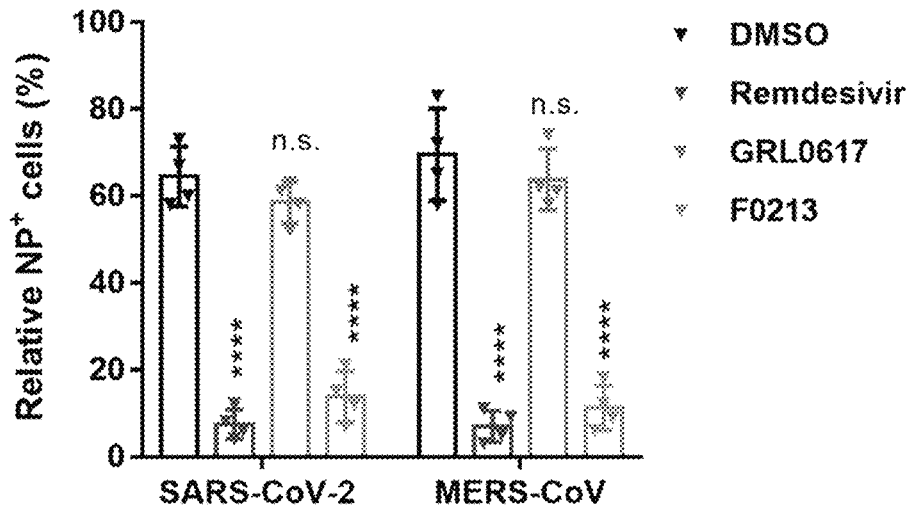
Figure 7A:
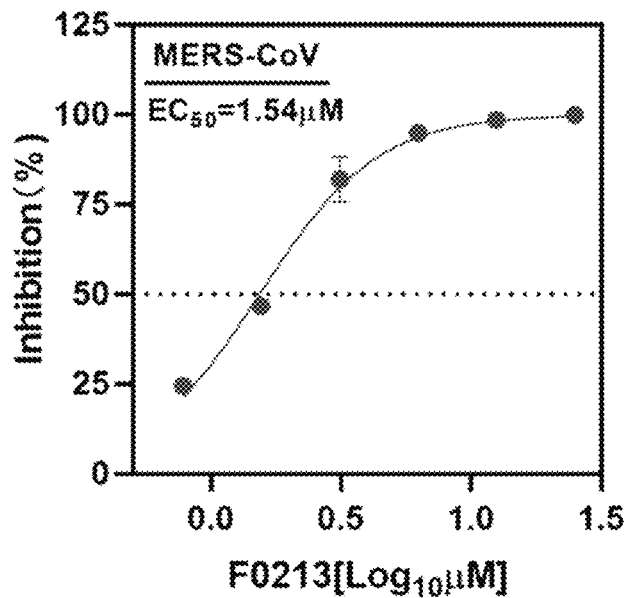
FIGS. 7A-7D Anti-MERS-CoV activity and cytotoxicity measurement of F0213. Anti-MERS activity of F0213 (FIG. 7A), F0326 (FIG. 7B), and GRL0617 (FIG. 7C).
Figure 7B:
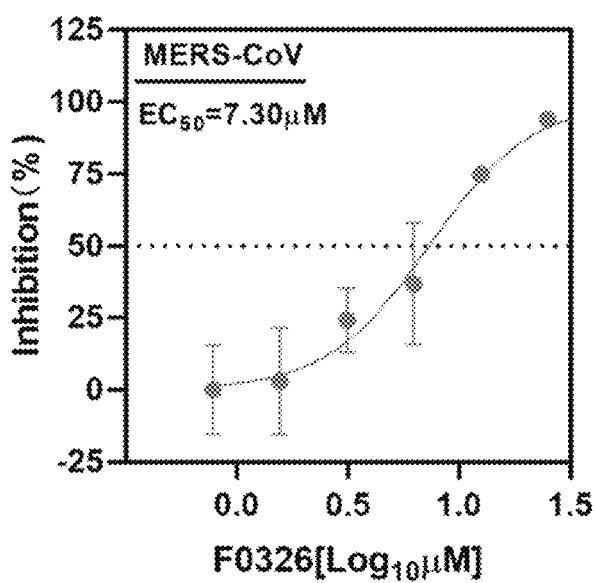
Figure 7C:
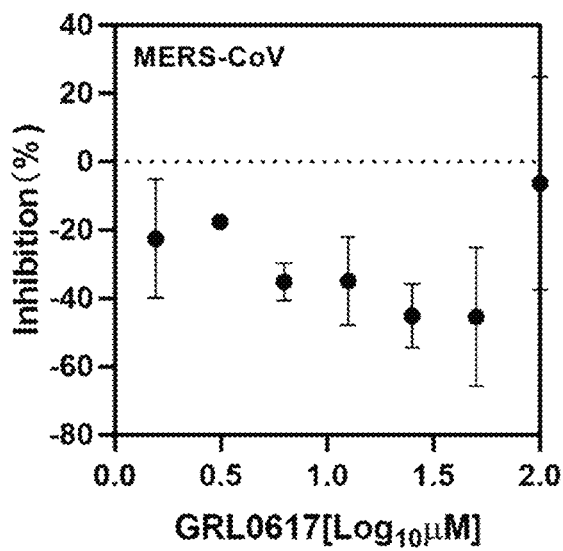

To prioritize the compounds, we performed antiviral assessment with live SARS-CoV-2. Apparently, F0213 ($EC_{50}$=4.5 µM) and F0326 ($EC_{50}$=7.6 µM) harbor anti-SARS-CoV-2 activity at non-toxic concentrations, whereas F0393 showed considerable cytotoxicity when >10 µM was applied (FIGS. 1D-1F). Considering the lowest $EC_{50}$s of F0213 against both SARS-CoV-2 and MERS-CoV, F0213 was chosen for subsequent characterization (FIGS. 7A-7C). The antiviral potency of F0213 was also evidenced by the immunofluorescence staining of SARS-CoV-2 or MERS-CoV NP antigen that significant inhibition of virus replication were visualized after either Remdesivir or F0213 treatment, while marginal virus suppression was observed when GRL0617 (20 µM) was utilized in SARS-CoV-2-infected or MERS-CoV-infected Vero cells (FIG. 1G and FIG. 7C).

Example 2—F0213 is a Pan-Coronavirus Inhibitor

Figure 2A:
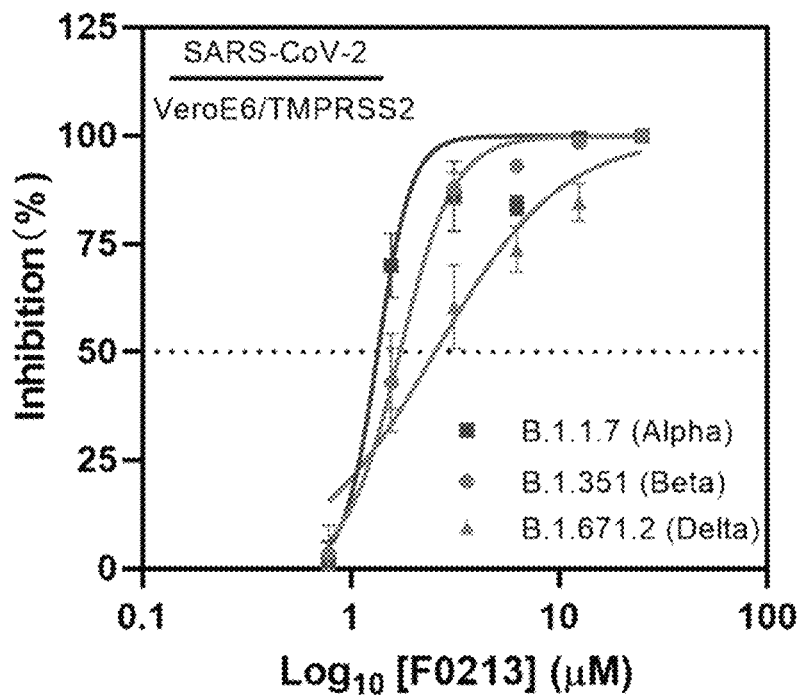
FIGS. 2A-2C F0213 inhibits a broad-spectrum of human-pathogenic CoVs replication in human cellular models.
Figure 2B:
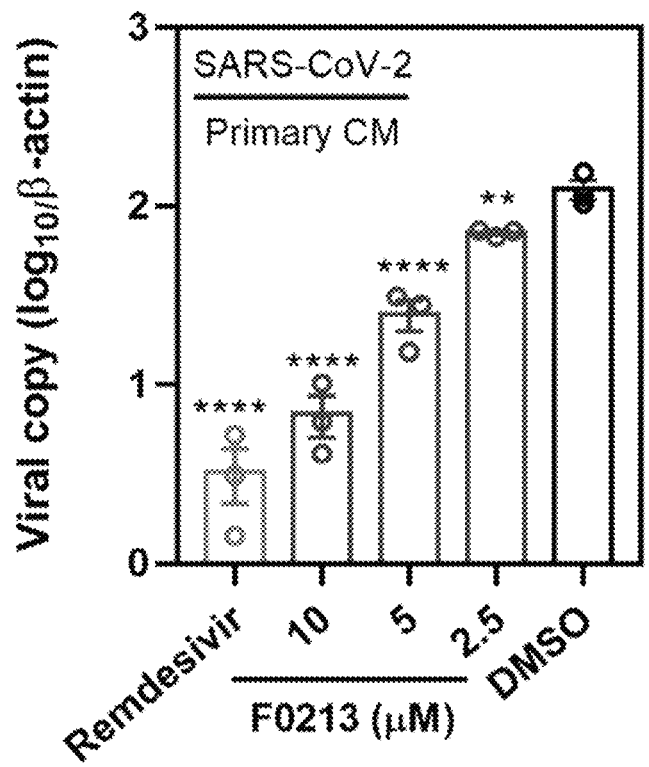
Figure 2C:
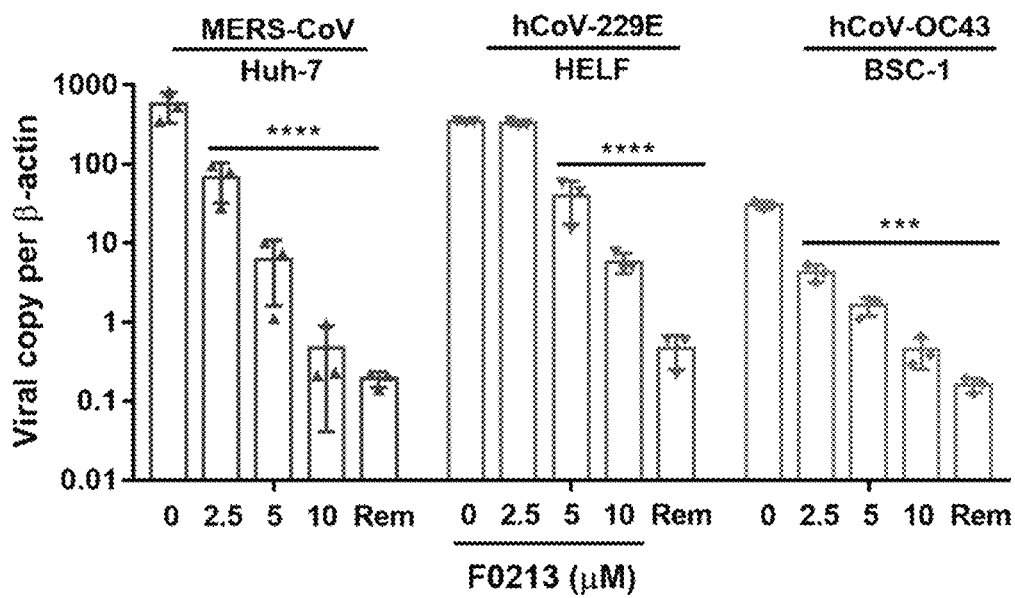
Figure 7D:
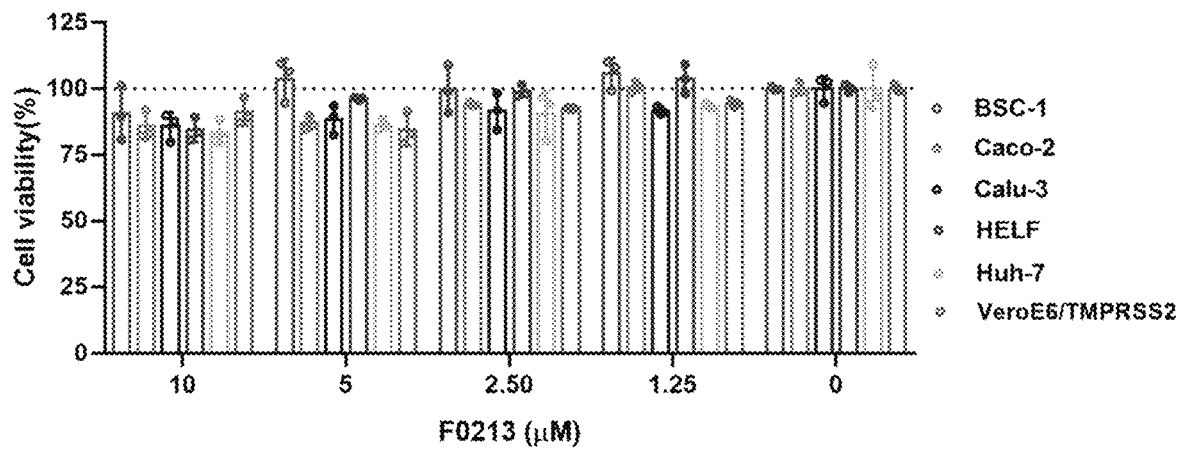

To examine the antiviral efficacy of F0213 against SARS-CoV-2 variants of concern (VOC), viral load reduction assays were performed utilizing the emerging B.1.1.7 (Alpha), B.1.351 (Beta) and B.1.617.2 (Delta) on VeroE6/TMPRSS2 cells. As expected, addition of F0213 suppressed replication of each VOC in a dose-dependent manner, exhibiting an $EC_{50}$ ranging from 2.2-4.8 µM (FIG. 2A). We then characterized the antiviral activity of F0213 in cardiomyocytes derived human embryonic stem cells (CM), which are more physiologically relevant and robustly support SARS-CoV-2 replication. F0213 treatment reduced the SARS-CoV-2 viral yields to more than 1 log 10, indicating its potential utility for amelioration of SARS-CoV-2 induced cardiac pathogenesis[7] (FIG. 1B). To explore whether F0213 confers cross-protection against other epidemic and seasonal coronaviruses, we performed viral-load reduction assays for MERS-CoV, hCoV-229E and hCoV-OC43 in corresponding cell lines that support virus replication. Viral yields in cell culture supernatants were decreased by about 3 log 10 in Huh-7 cells infected with MERS-CoV, by about 2 log 10 in human embryonic lung fibroblasts infected with hCoV-229E and by around 1.5 log 10 in monkey BSC-1 cells infected with hCoV-OC43 (FIG. 2C). F0213 showed negligible cytotoxicity in the matching cell lines as described above for pan-coronavirus inhibitory evaluation (FIG. 7D). Overall, F0213 exhibited broad-spectrum anti-coronavirus efficacy, and antagonized SARS-CoV-2 replication in a human primary cell model.

Example 3—F0213 Antagonizes PLpro-Mediated Innate Suppression

Figure 3A:
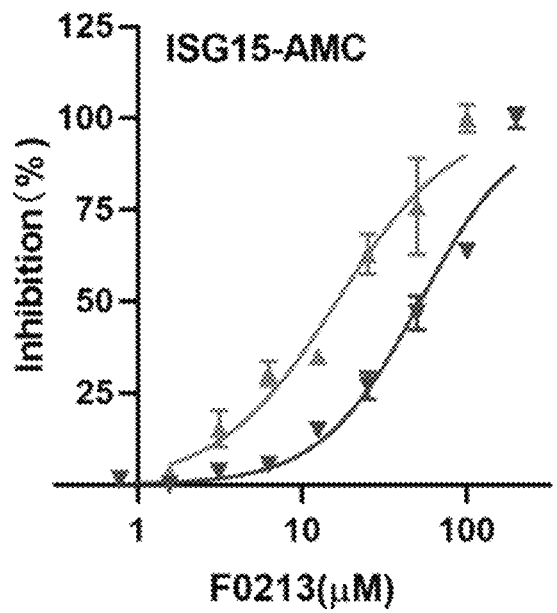
FIGS. 3A-3F F0213 antagonize PL-pro-mediated innate suppression. F0213 inhibited cleavage of ISG15-AMC (FIG. 3A) and Ubiquitin-AMC (FIG. 3B) that mediated by MERS-CoV PLpro and SARS-CoV-2 PLpro Data are mean±s.d. n=3 independent experiments.
Figure 3B:
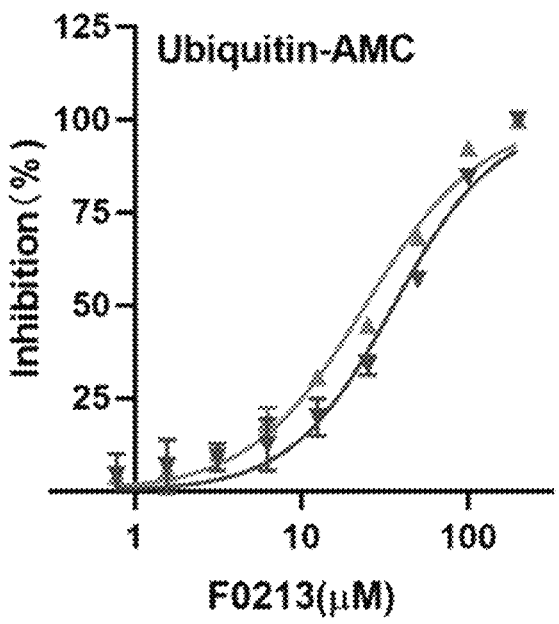
Figure 3C:
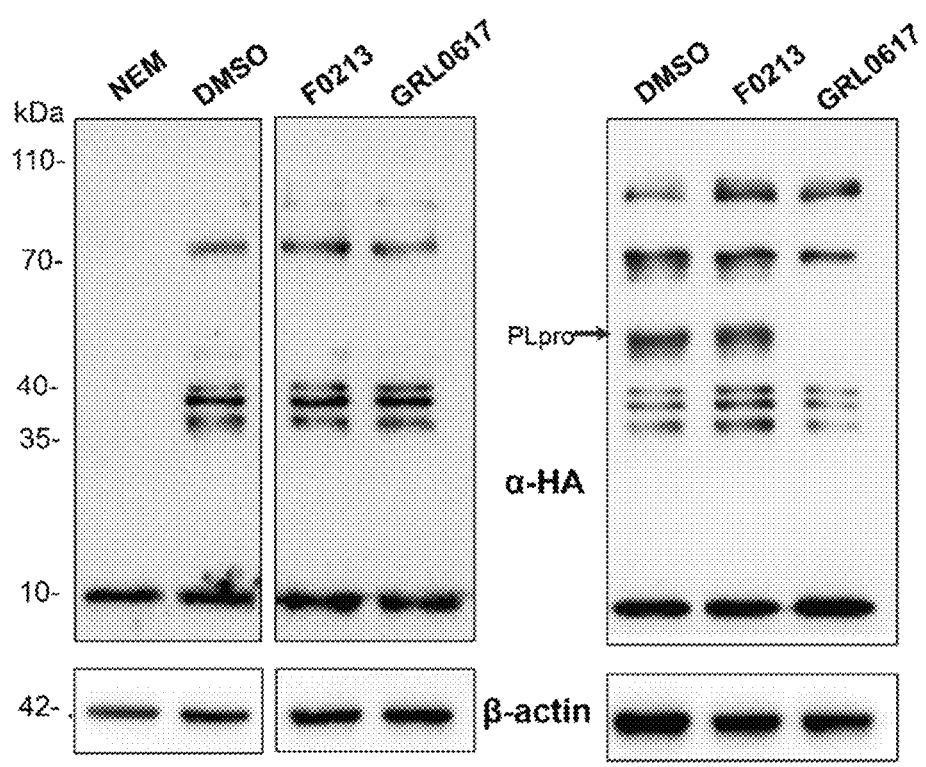
Figure 3D:
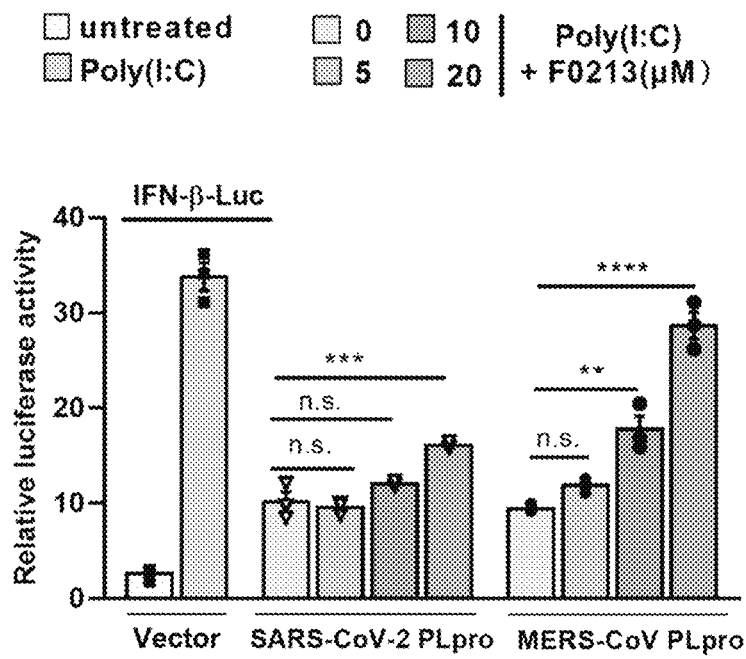
Figure 3E:
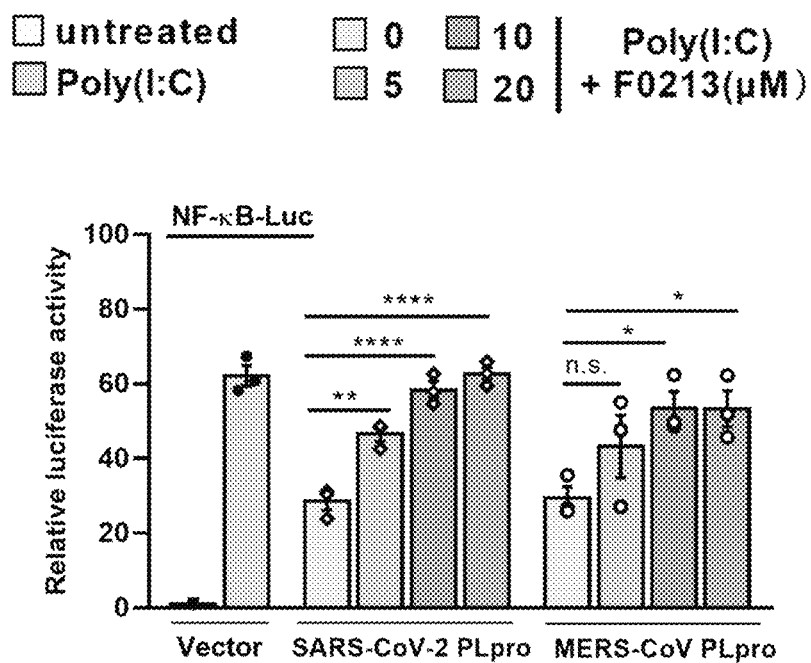
Figure 3F:
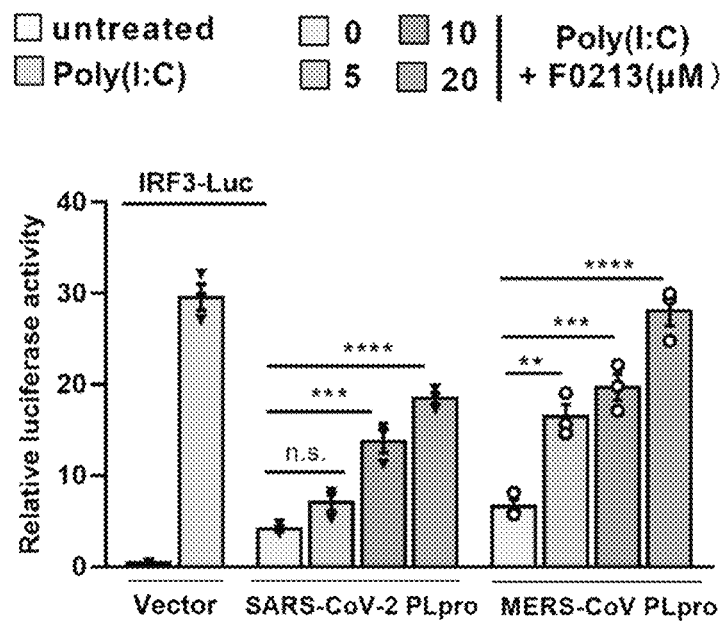
Figure 8A:
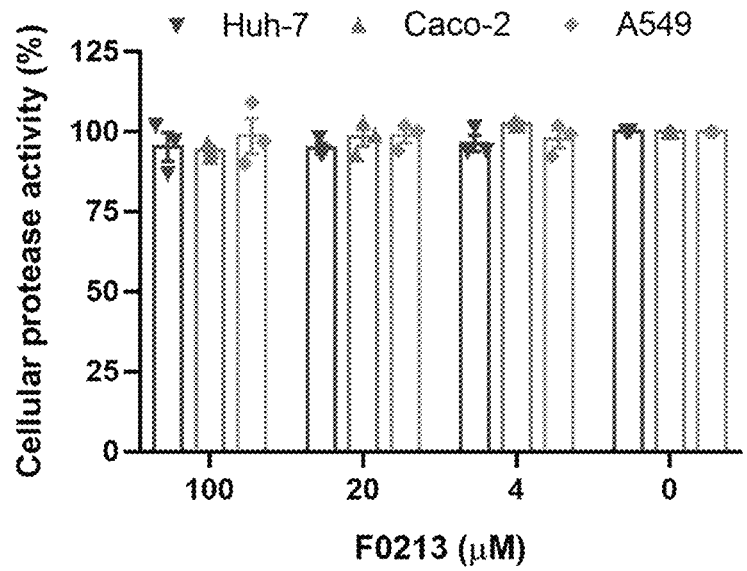
FIGS. 8A-8E Exploration of possible effect of F0213 on host cells.

PLpro has the function of stripping ubiquitin and ISG15 from host-cell proteins to aid coronaviruses in their evasion of the host innate immune responses[5]. To explore the role of F0213 to rewire such process, cleaving activity against ubiquitin-AMC and ISG15-AMC substrates were titrated with different concentrations of F0213. Generally, MERS-CoV-PLpro showed higher sensitivity than that SARS-CoV-2 upon the drug treatment, corroborating that F0213 exhibits a lower antiviral $EC_{50}$ against MERS-CoV than SARS-CoV-2 (FIGS. 3A-3B). Structural and functional studies have revealed that PLpro is homologous to human deubiquitinating enzymes (DUBs) thus cleaving ubiquitin and ubiquitin-like modifiers such as ISG15[8]. To examine the specificity of F0213 for PLpro over human DUBs, we probed the ability of human DUBs from cellular lysates to be modified by the active-site-directed probe HA-Ub-vinyl sulfone (VS) in the presence and absence of F0213. In principle, cellular DUBs become modified when treated with HA-Ub-VS thus can be visualized by Western blot analysis by using an anti-HA antibody. Apparently, treatment with a positive control inhibitor NEM diminished the modification of HA-Ub-VS on DUBs derived from Caco-2 cells, whereas no change was noted in the immunoblot pattern upon F0213 treatment FIG. 3C). When PLpro was added to the lysate, it too underwent modification by the HA-Ub-VS, but unlike the cellular DUBs, its modification by the VS was almost completely eliminated in the presence of GRL0617 but not F0213 (FIG. 3F). The results suggest that F0213 is a specific PLpro inhibitor that distinguish from GRL0617's mode of action. Utilizing a fluorescent-casein substrate, in addition, a wide variety of cellular proteases including serine proteases (trypsin, chymotrypsin, thrombin, plasmin, elastase, subtilisin), cysteine proteases (papain, cathepsin B) and acid proteases (thermolysin, pepsin) were not affected by F0213 (FIG. 8A).

Figure 8B:
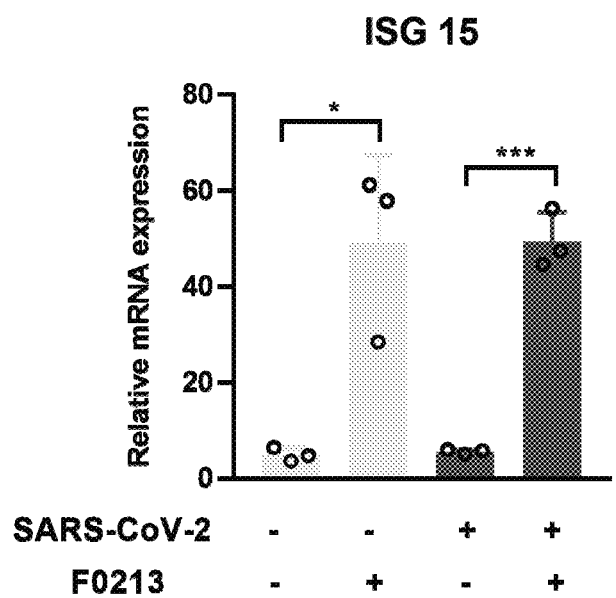
Figure 8C:
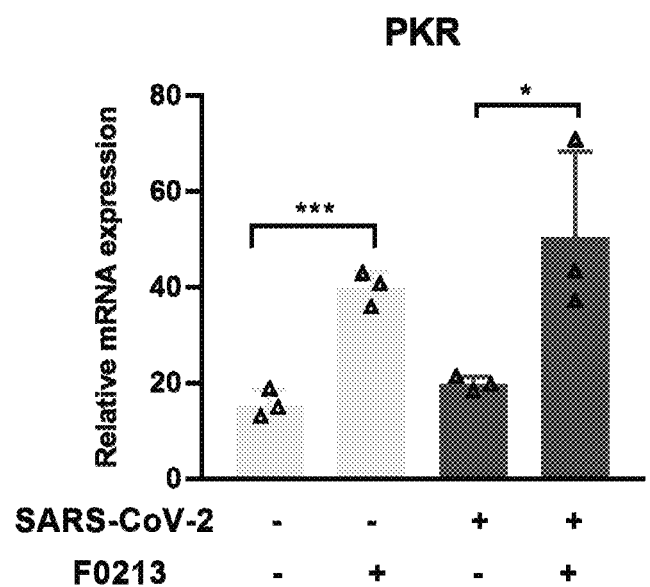
Figure 8D:
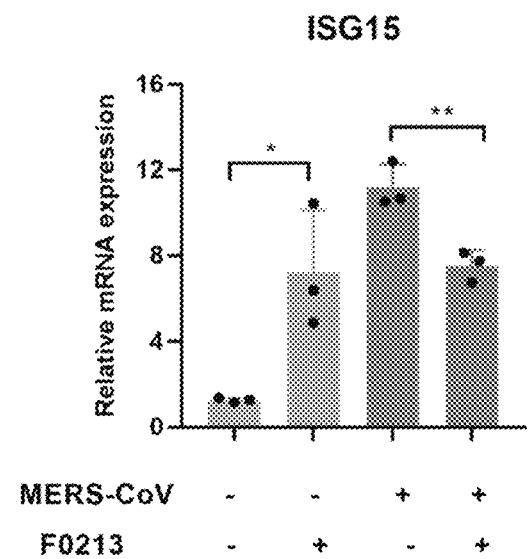
Figure 8E:
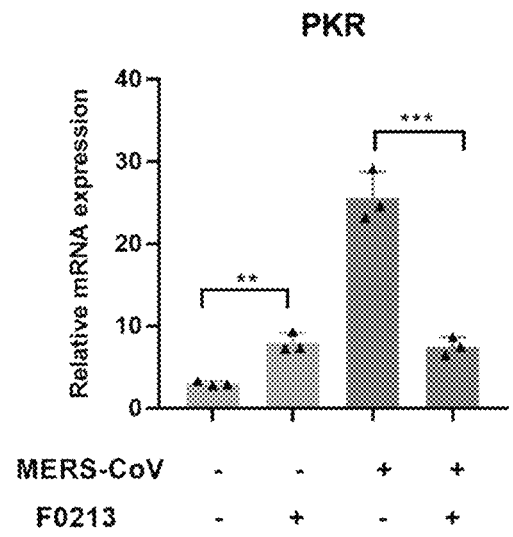

To ascertain the role of F0213 to antagonize the PLpro-mediated IFN suppression, luciferase reporter assays reflecting the transcriptional activation of IFN-β, IRF3 and NF-κB genes were performed. Both SARS-CoV-2 and MERS-CoV attenuated IFN response, while addition of F0213 rescued the genes expression in a dose-dependent manner (FIGS. 3D-3F). In an infectious scenario, F0213 treatment significantly enhanced the expression of IFN-responsive genes ISG15 and PKR in SARS-CoV-2-infected Caco-2 cells (FIGS. 8B-8C). By contrast, transcription levels of ISG15 and PKR were reduced by F0213 in a MERS-CoV-infected Huh-7 cell model (FIGS. 8D-8E). The differential patterns might be explained by the previous report that SARS-CoV-2 infection in animal models and in COVID-19 patients is correlated with low IFN type I and type III responses[9], whereas MERS-CoV generally elevated IFN response after infection[10]. F0213, predominantly as a virus-targeting inhibitor, thus reverse the CoVs-induced IFN responses. In the absence of CoVs infection, intriguingly, F0213 potentiated the cellular antiviral signaling in both Caco-2 and Huh-7 cells (FIGS. 8B-8E). These findings suggest that F0213 may not only serve as a PLpro inhibitor to reverse the virus-induced immunosuppression, but also as a modulator to prime host antiviral response.

Figure 4A:
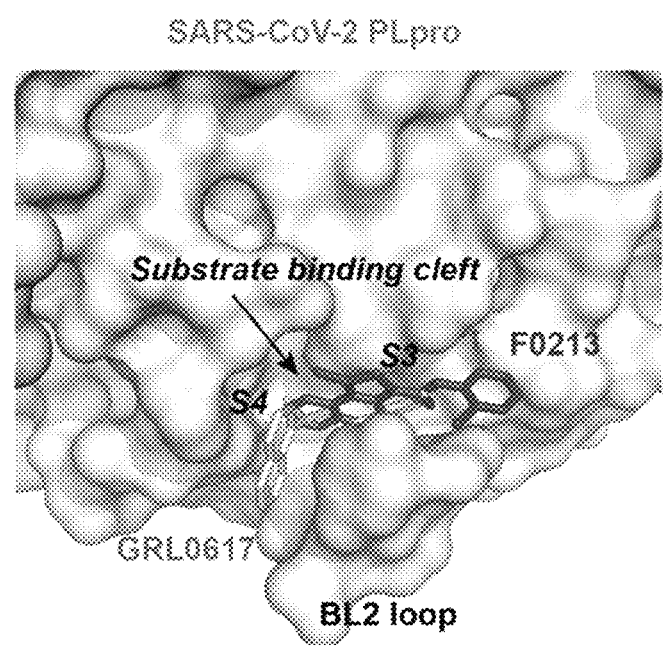
FIGS. 4A-4F Molecular docking analysis of F0213 with SARS-CoV-2 and MERS-CoV PLpro proteases.
Figure 4B:
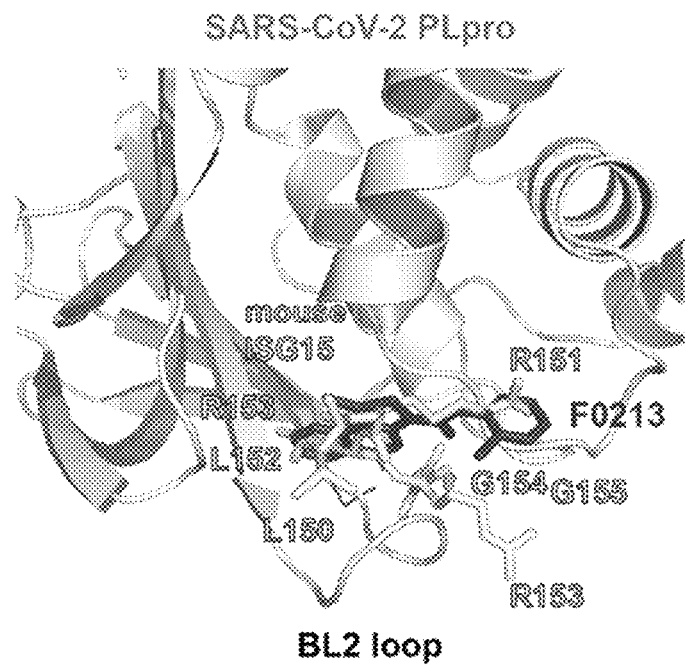
Figure 4C:
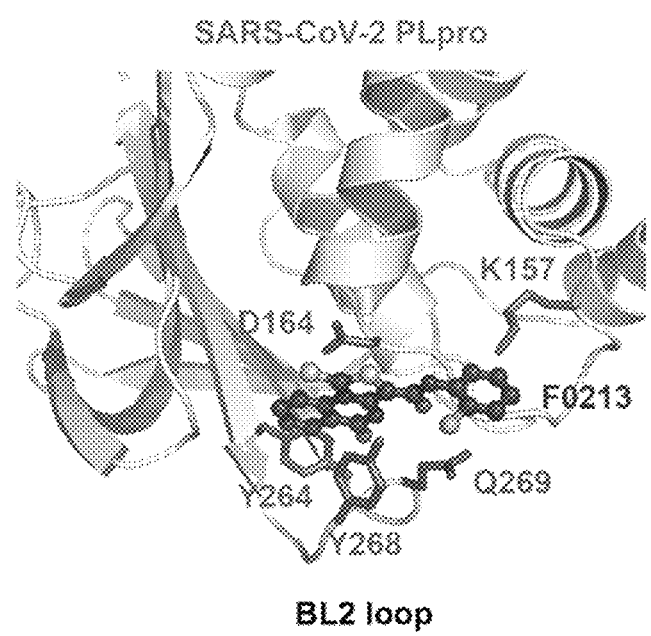
Figure 4D:
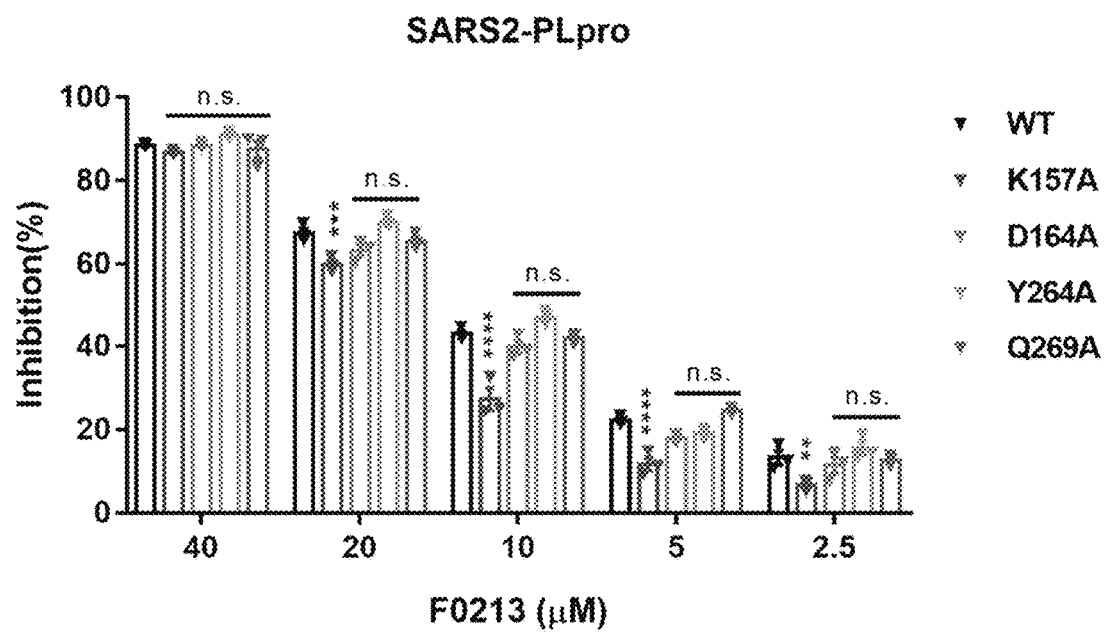
Figure 4E:
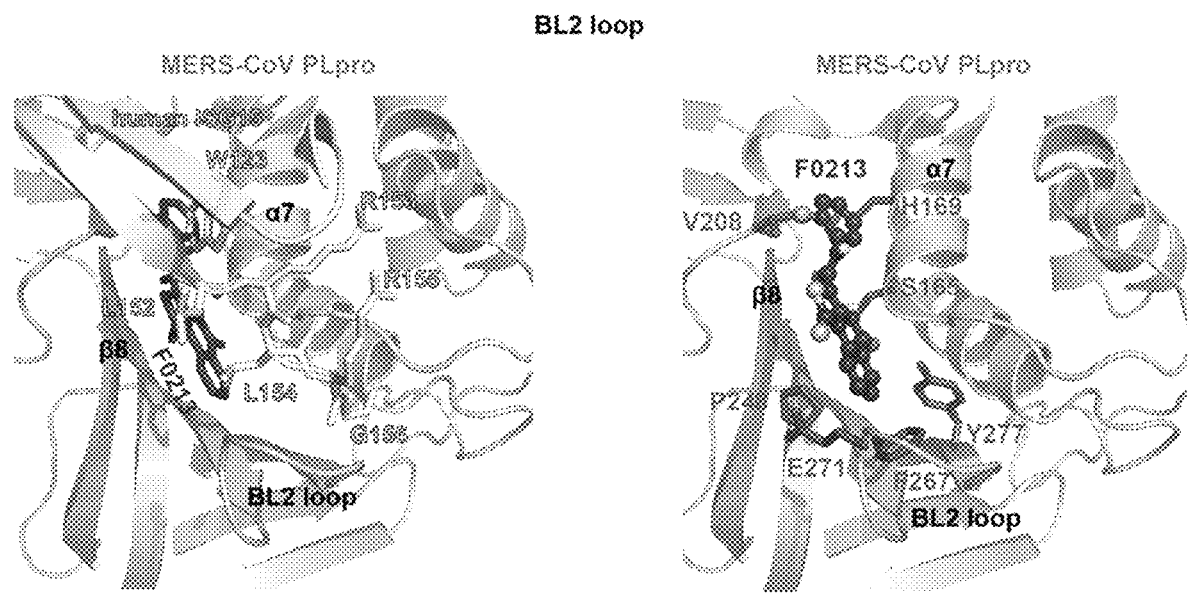
Figure 9:
FIG. 9 SDS-PAGE gel image of WT and mutant SARS-2-PLpro as well as WT and mutant MERS-PLpro used in this study (1.5 μg/lane).
Figure 9:
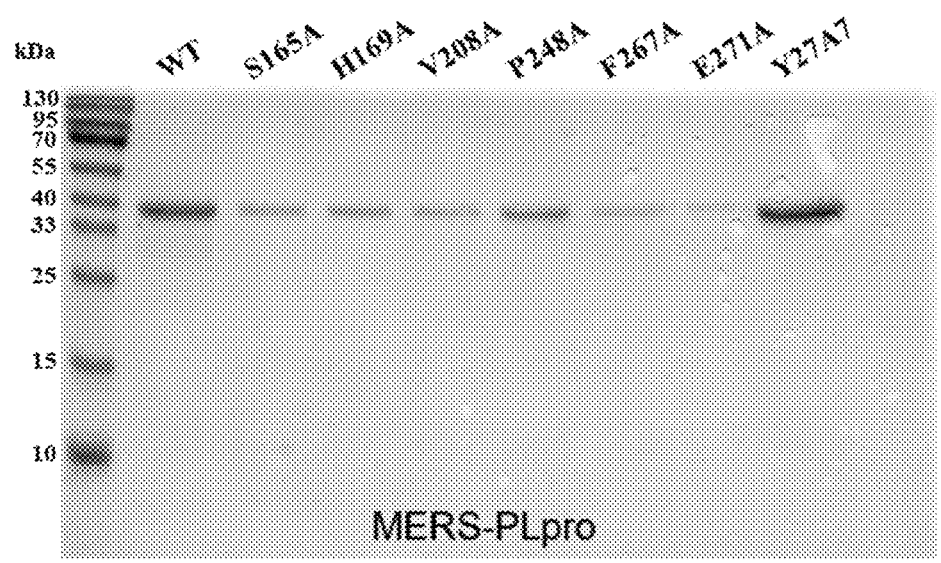
Figure 10A:
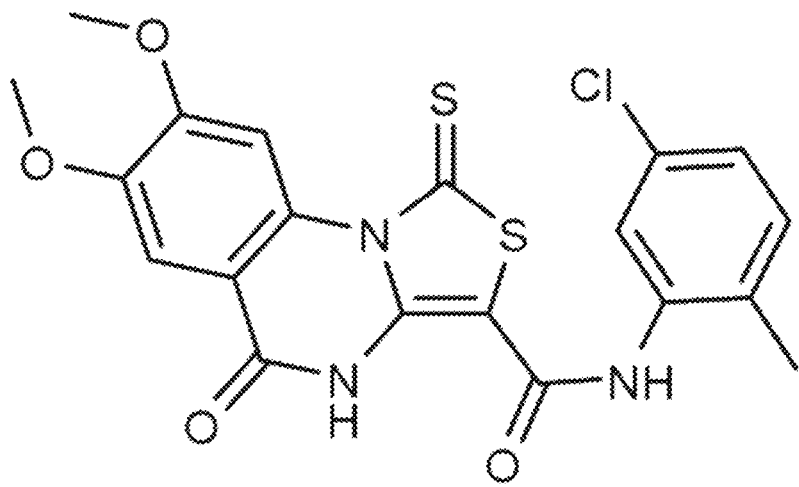
FIGS. 10A-10B. Dose-response relationships of selected antiviral compounds, depicting infectivity (colored), cytotoxicity (black), and IC50 values of Compound F0326 (FIG. 10A) and compound F0393 (FIG. 10B).
Figure 10A:
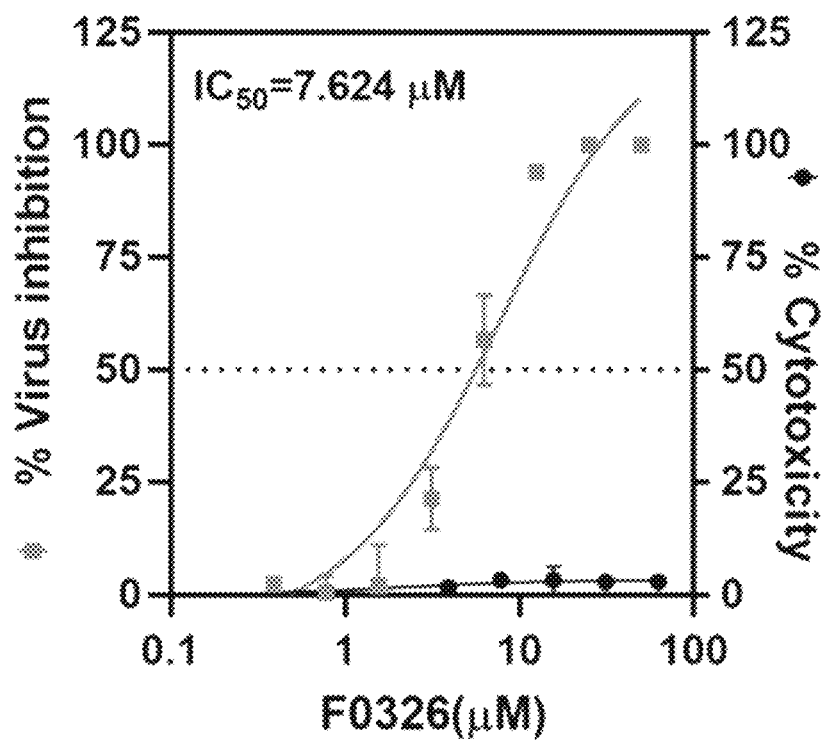
Figure 10B:
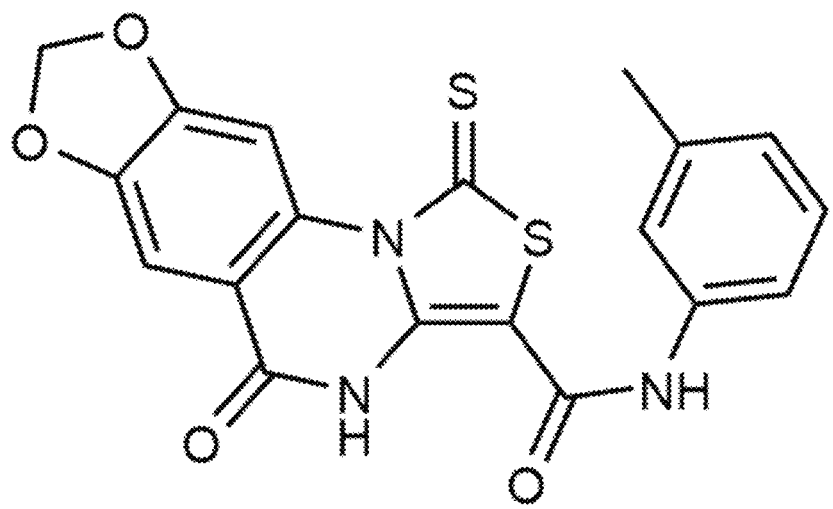
Figure 10B:
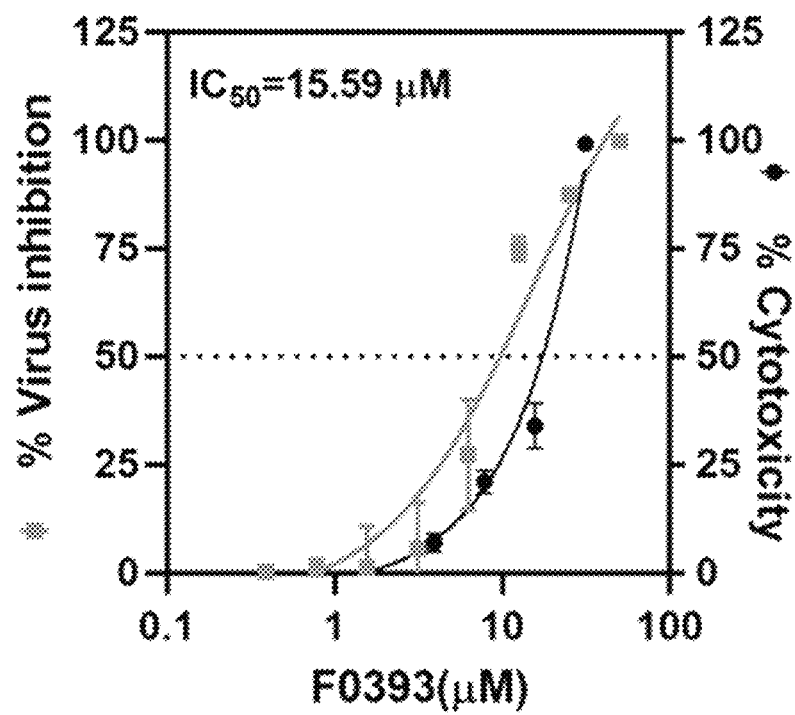

Example 4—F0213 Exhibits Distinct Binding Modes Against SARS-CoV-2-PLpro and MERS-CoV-PLpro To reveal the structural mechanism underlying the action of F0213, we sought to co-crystallize the compound in complex with SARS-CoV-2 PLpro and MERS-CoV PLpro. However, we were unable to obtain structure of neither complex. The difficulty of crystallization was partially due to the relatively low solubility of F0213. Thus, we used software Autodock Vina for docking the compound to the structures of different PLpros. With a search space covering the substrate binding pockets of SARS-CoV-2 PLpro (PDB ID: 7 JRN), we identified 20 binding modes of F0213, the best of which had a predicted binding affinity −8.0 kcal/mol. The interaction between F0213 and SARS-CoV-2 PLpro involves five key residues: K157, D164, Y264, Y268 and Q269. Our model predicted that F0213 was placed inside a narrow substrate binding cleft near the active site of the protease (FIGS. 4A-4C). The thiazolo-quinazoline rings of F0213 accommodates in the S3-S4 pockets of SARS-CoV-2 and attaches to the blocking loop 2 (BL2 loop), possibly via π-π stacking with Y268 on the top of the BL2 loop. Structure superimposition revealed that the narrow cleft is also occupied by the benzenamine moiety of GRL0617 or the leucine (P4) of the LRGG motif of ISG15 (PDB ID: 6 YVA). One the other hand, the chlorophenyl moiety of F0213 overlays with the position of R151 of the bound ISG15, an important residue for ISG15 mediated antiviral immune response[11]. To validate, we employed site-mutagenesis to construct individual SARS2-PLpro mutant. All constructs can be successfully expressed in a prokaryotic expression, excepting that substitution Y268A abolished the PLpro cleavage activity (FIG. 9). To examine the inhibitory activity of F0213 against each mutant, protease cleavage assay using RLRGG-AMC substrate was conducted. Consistently, only K157A substitution significantly diminished the inhibitory potency of F0213 while the others were not (p<0.01, FIG. 4D). Collectively, the predicted binding mode of F0213 suggests K157 the key amino acid residue mediating the compound and SARS2-PLpro interaction.

Figure 4F:
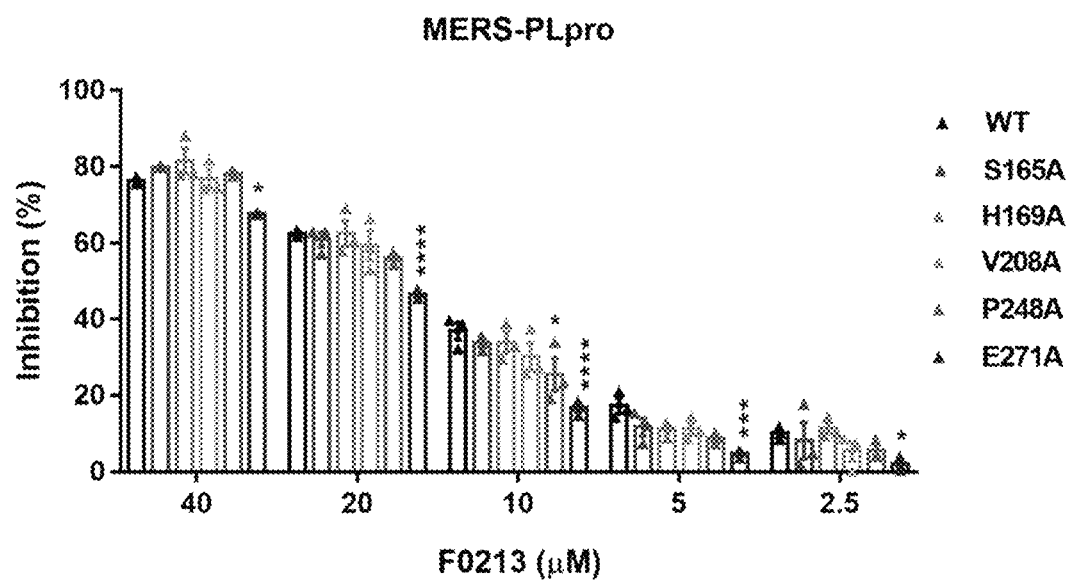

Using the similar approach, we docked F0213 to a crystal structure of MERS-CoV PLpro (PDB ID: 4 RNA) and identified 20 binding modes of the compound. The best binding mode had a predicted binding affinity −7.9 kcal/mol and involved seven key residues of MERS-CoV PLpro: S165, H169, V208, P248, F267, E271 and Y277. The predicted binding mode of F0213 with MERS-CoV PLpro differs significantly from that with SARS-CoV-2 PLpro. Instead of attaching to the BL2 loop, F0213 is inserted to a shallow cleft formed between α7 and μ8 of MERS-CoV PLpro. Superimposing our model with human ISG15-MERS-CoV PLpro complex reveal that the chlorophenyl moiety of the modelled F0213 overlays with residue W123 of MERS-CoV PLpro, which is an important residue mediating hydrophobic interaction between MERS-CoV PLpro and ISG15[12]. Biochemical validation showed that either F267A or Y277A substitution diminish the MERS-PLpro enzyme activity, whereas E271A substitution compromised the inhibitory potency of F0213 against MERS-PLpro (FIG. 4F). Taken together, the results indicate a distinct mode of inhibition of F0213 between SARS2-PLpro and MERS-PLpro.

Finally, isothermal titration calorimetry (ITC) was utilized to investigate the binding affinity between F0213 and different PLpros.

Example 5—F0213 Improves Lung Pathogenesis in a SARS-CoV-2 Hamster Model

Figure 5A:
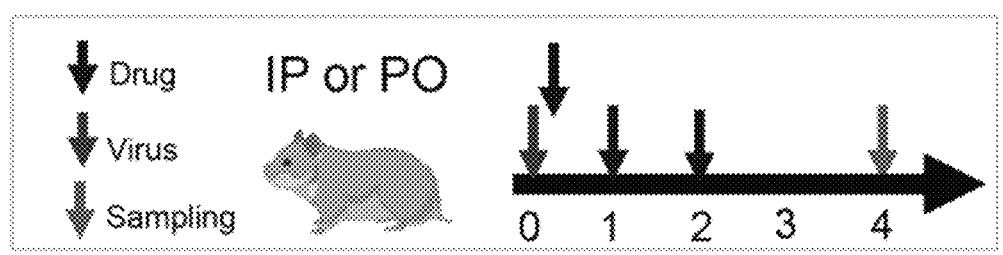
FIGS. 5A-5E F0213 improve lung pathogenesis a SARS2-infected hamster model.
Figure 5B:
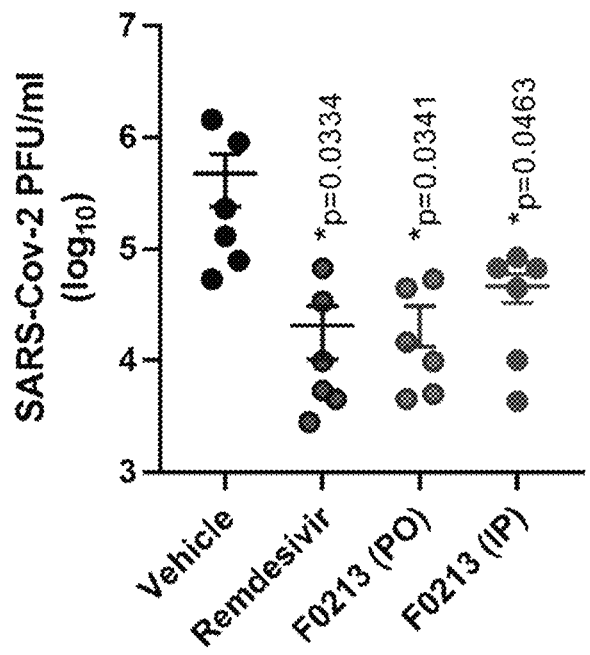
Figure 5C:
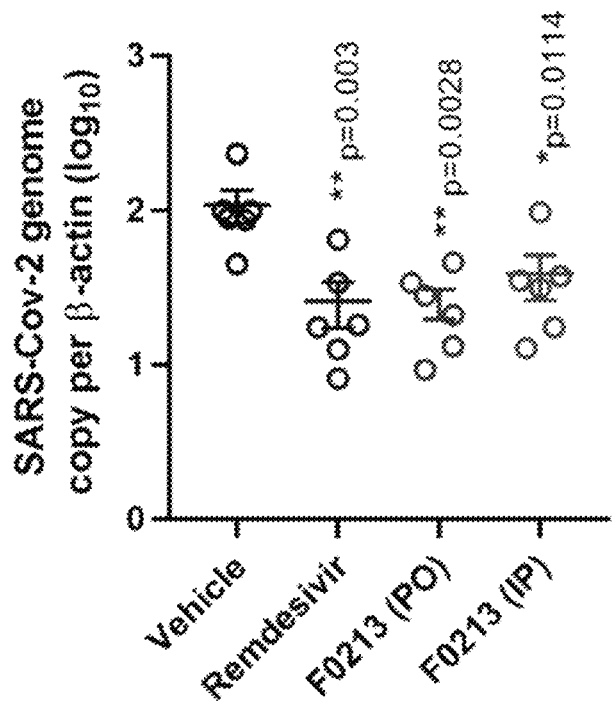
Figure 5D:
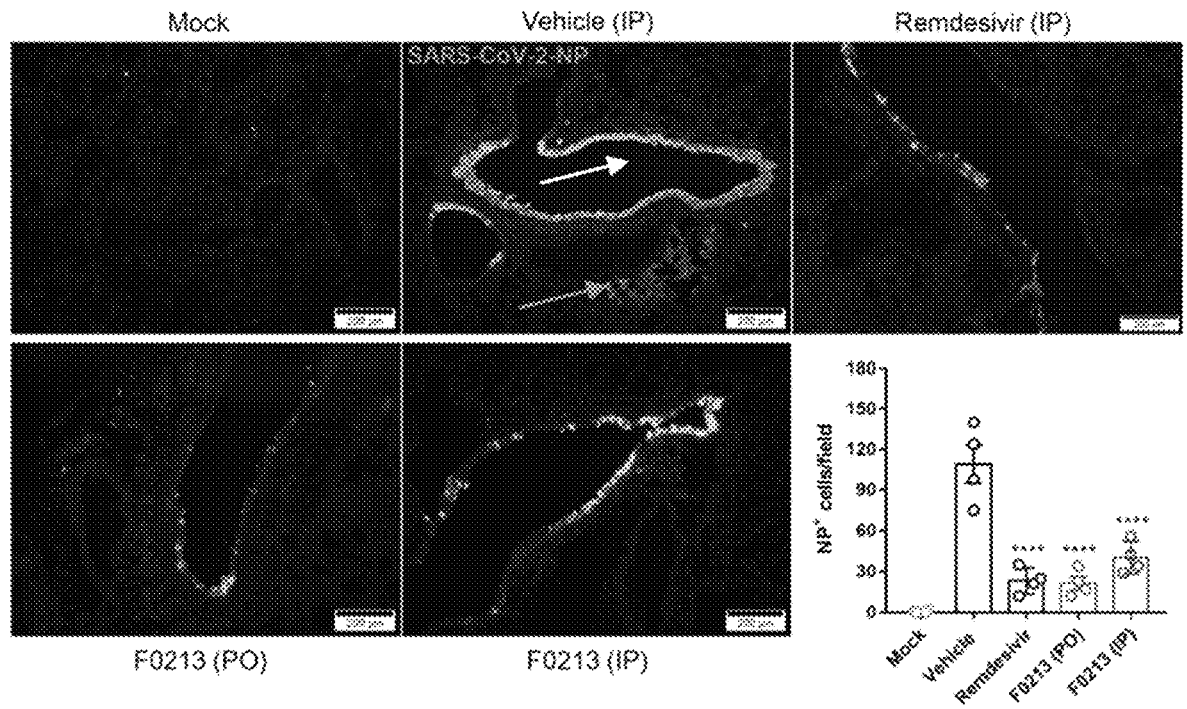
Figure 5E:
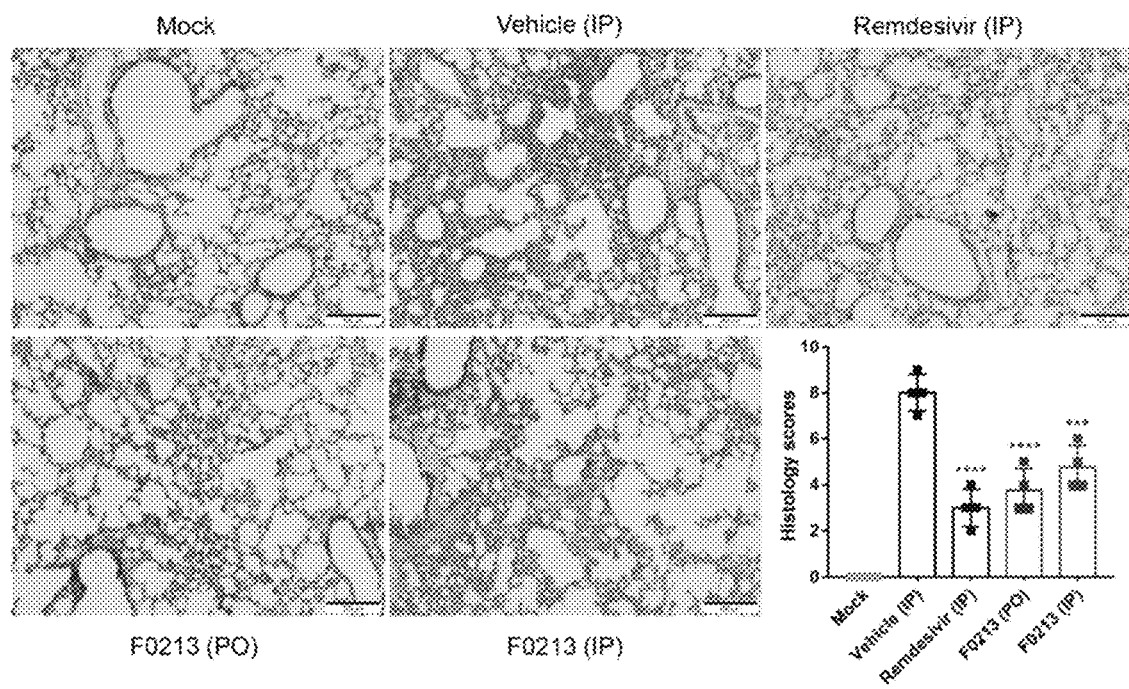

Next, we utilized a golden Syrian hamster model to further evaluate the anti-SARS-CoV-2 activity of F0213 in vivo[13]. Therapeutic regimen using either oral (PO) or intraperitoneal (IP) administration of F0213 (5 mg/kg/day) was applied, with the first dose given at 6 hpi and once daily for consecutive 3 days (FIG. 5A). On 4 dpi when viral loads peaked and there were substantial histopathological changes, F0213 decreased the virus plaque-forming units in lung tissues by about 1-2 log 10 (FIG. 5B). Consistently, the suppression of SARS-CoV-2 genome copies in the lungs were observed in F0213—or Remdesivir-treated hamsters, and indicating a superior efficacy via PO route than that of IP injection (FIG. 5C). Immunofluorescence staining suggested abundant SARS-CoV-2 N expression (green) as shown in diffuse alveolar areas and in the focal bronchiolar epithelial cells of the vehicle-treated hamster lungs, whereas both Remdesivir- and F021-treated groups exhibited reduced N expression (FIG. 5D). The severity of lung damage was also examined by performing hematoxylin and eosin (H & E) staining. Notably, vehicle-treated group developed certain degree of alveolar consolidation and cell infiltrations. By contrast, F0213 or Remdesivir-treated lungs exhibited an improved morphology and milder infiltrations (FIG. 5E). Overall, F0213 conferred protection against SARS-CoV-2 challenge in the hamster model by reducing virus replication and associated inflammatory damage.

Example 6—F0213 Protects Mouse from Lethal MERS-CoV Challenge

Figure 6A:
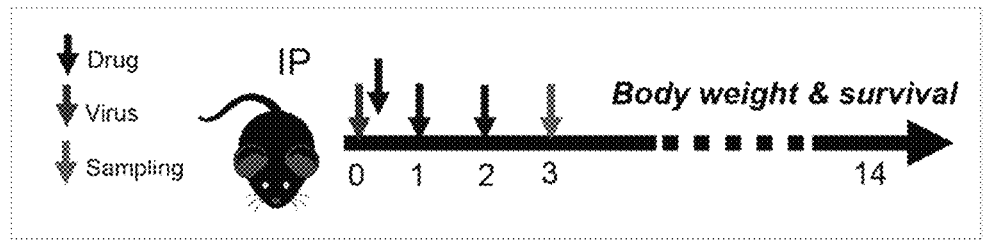
FIGS. 6A-6E F0213 protects mouse from lethal MERS-CoV challenge.
Figure 6B:
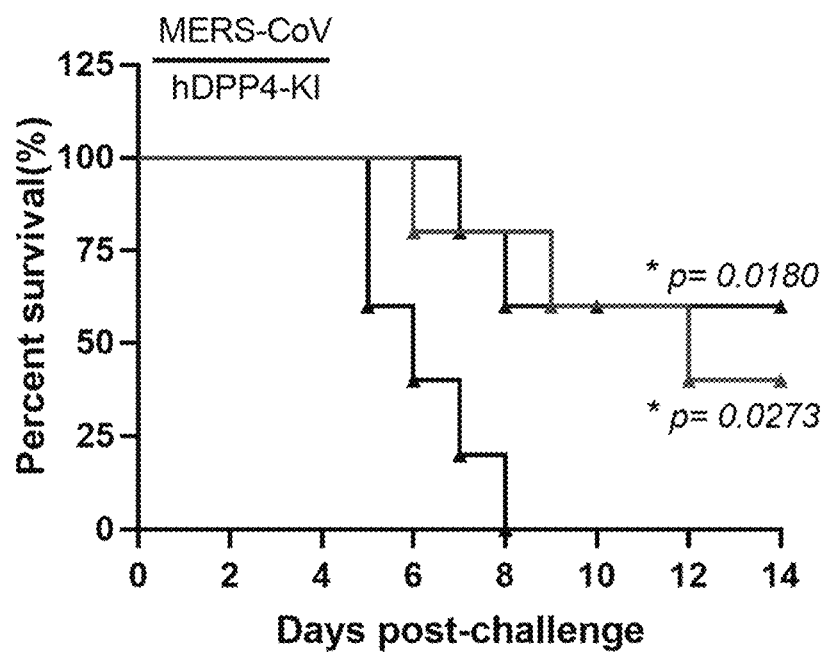
Figure 6C:
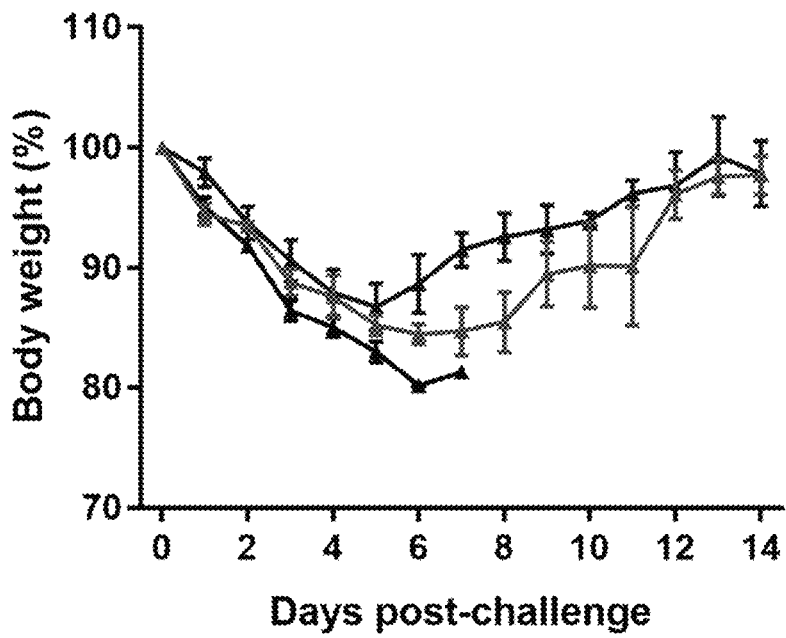
Figure 6D:
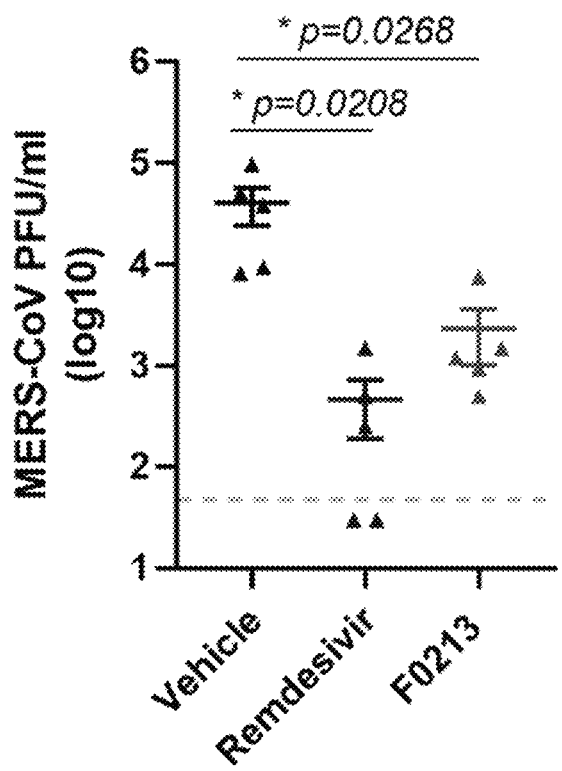
Figure 6E:
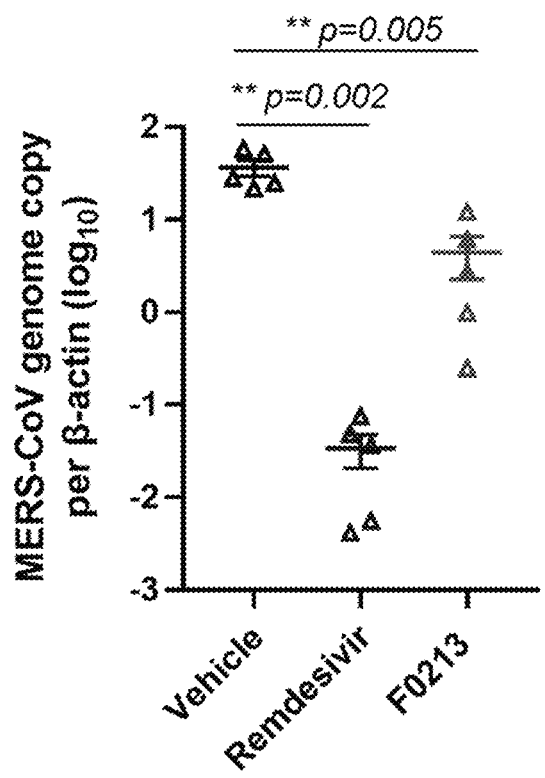

To ascertain the anti-MERS-CoV potency of F0213 in vivo, we employed a lethal human Dipeptidyl peptidase-4 (DPP4) knock-in mouse model[14]. We challenged mice with 2000 plaque-forming units (PFU) of mouse-adapted MERS-CoV, followed by IP delivery of F0213 (20 mg/kg/day) or Remdesivir (20 mg/kg/day) at 6 hpi, 24 hpi and 48 hpi, respectively (FIG. 6A). All vehicle-treated mice died on or before 8 dpi, whereas F0213 conferred substantial better survival against (40% versus 0%) as well as delayed death (FIG. 6B). Generally less body weight loss were recorded in both F0213 and Remdesivir-treated mouse groups, which started to rebound at 8 dpi and 6 dpi, respectively (FIG. 6C). The improved clinical disease was also evidenced by >1 log $_{10}$ reduction of both live virus plaque-forming units and viral genome copies on 3 dpi and in mouse lungs (FIG. 6D). Together, F0213 effectively protected animals challenged with SARS-CoV-2 or MERS-CoV by reducing virus replication.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Chan, J. F.; Lau, S. K.; To, K. K.; Cheng, V. C.; Woo, P. C.; Yuen, K. Y., Middle East respiratory syndrome coronavirus: another zoonotic betacoronavirus causing SARS-like disease. *Clin Microbiol Rev* 2015, 28 (2), 465-522.
2. Barretto, N.; Jukneliene, D.; Ratia, K.; Chen, Z.; Mesecar, A. D.; Baker, S. C., The papain-like protease of severe acute respiratory syndrome coronavirus has deubiquitinating activity. *J Virol* 2005, 79 (24), 15189-98.
3. Klemm, T.; Ebert, G.; Calleja, D. J.; Allison, C. C.; Richardson, L. W.; Bernardini, J. P.; Lu, B. G.; Kuchel, N. W.; Grohmann, C.; Shibata, Y.; Gan, Z. Y.; Cooney, J. P.; Doerflinger, M.; Au, A. E.; Blackmore, T. R.; van der Heden van Noort, G. J.; Geurink, P. P.; Ovaa, H.; Newman, J.; Riboldi-Tunnicliffe, A.; Czabotar, P. E.; Mitchell, J. P.; Feltham, R.; Lechtenberg, B. C.; Lowes, K. N.; Dewson, G.; Pellegrini, M.; Lessene, G.; Komander, D., Mechanism and inhibition of the papain-like protease, PLpro, of SARS-CoV-2. *EMBO J* 2020, 39 (18), e106275.
4. Shin, D.; Mukherjee, R.; Grewe, D.; Bojkova, D.; Baek, K.; Bhattacharya, A.; Schulz, L.; Widera, M.; Mehdipour, A. R.; Tascher, G.; Geurink, P. P.; Wilhelm, A.; van der Heden van Noort, G. J.; Ovaa, H.; Muller, S.; Knobeloch, K. P.; Rajalingam, K.; Schulman, B. A.; Cinatl, J.; Hummer, G.; Ciesek, S.; Dikic, I., Papain-like protease regulates SARS-CoV-2 viral spread and innate immunity. *Nature* 2020, 587 (7835), 657-662.
5. Baez-Santos, Y. M.; Mielech, A. M.; Deng, X.; Baker, S.; Mesecar, A. D., Catalytic function and substrate specificity of the papain-like protease domain of nsp3 from the Middle East respiratory syndrome coronavirus. *J Virol* 2014, 88 (21), 12511-27.
6. Ratia, K.; Pegan, S.; Takayama, J.; Sleeman, K.; Coughlin, M.; Baliji, S.; Chaudhuri, R.; Fu, W.; Prabhakar, B. S.; Johnson, M. E.; Baker, S. C.; Ghosh, A. K.; Mesecar, A. D., A noncovalent class of papain-like protease/deubiquitinase inhibitors blocks SARS virus replication. *Proc Natl Acad Sci U S A* 2008, 105 (42), 16119-24.
7. Madjid, M.; Safavi-Naeini, P.; Solomon, S. D.; Vardeny, O., Potential Effects of Coronaviruses on the Cardiovascular System: A Review. *JAMA Cardiol* 2020, 5 (7), 831-840.
8. Ratia, K.; Saikatendu, K. S.; Santarsiero, B. D.; Barretto, N.; Baker, S. C.; Stevens, R. C.; Mesecar, A. D., Severe acute respiratory syndrome coronavirus papain-like protease: structure of a viral deubiquitinating enzyme. *Proc Natl Acad Sci USA* 2006, 103 (15), 5717-22.
9. Blanco-Melo, D.; Nilsson-Payant, B. E.; Liu, W. C.; Uhl, S.; Hoagland, D.; Moller, R.; Jordan, T. X.; Oishi, K.; Panis, M.; Sachs, D.; Wang, T. T.; Schwartz, R. E.; Lim, J. K.; Albrecht, R. A.; tenOever, B. R., Imbalanced Host Response to SARS-CoV-2 Drives Development of COVID-19. *Cell* 2020, 181 (5), 1036-1045 e9.
10. Inandiklioglu, N.; Akkoc, T., Immune Responses to SARS-CoV, MERS-CoV and SARS-CoV-2. *Adv Exp Med Biol* 2020, 1288, 5-12.
11. Giannakopoulos, N. V.; Arutyunova, E.; Lai, C.; Lenschow, D. J.; Haas, A. L.; Virgin, H. W., ISG15 Arg151 and the ISG15-Conjugating Enzyme UbE1L Are Important for Innate Immune Control of Sindbis Virus. *Journal of virology* 2009, 83 (4), 1602-1610.
12. Clasman, J. R.; Everett, R. K.; Srinivasan, K.; Mesecar, A. D., Decoupling deISGylating and deubiquitinating activities of the MERS virus papain-like protease. *Antiviral research* 2020, 174.
13. Chan, J. F.; Zhang, A. J.; Yuan, S.; Poon, V. K.; Chan, C. C.; Lee, A. C.; Chan, W. M.; Fan, Z.; Tsoi, H. W.; Wen, L.; Liang, R.; Cao, J.; Chen, Y.; Tang, K.; Luo, C.; Cai, J. P.; Kok, K. H.; Chu, H.; Chan, K. H.; Sridhar, S.; Chen, Z.; Chen, H.; To, K. K.; Yuen, K. Y., Simulation of the Clinical and Pathological Manifestations of Coronavirus Disease 2019 (COVID-19) in a Golden Syrian Hamster Model: Implications for Disease Pathogenesis and Transmissibility. *Clin Infect Dis* 2020, 71 (9), 2428-2446.
14. Li, K.; Wohlford-Lenane, C. L.; Channappanavar, R.; Park, J. E.; Earnest, J. T.; Bair, T. B.; Bates, A. M.; Brogden, K. A.; Flaherty, H. A.; Gallagher, T.; Meyerholz, D. K.; Perlman, S.; McCray, P. B., Jr., Mouse-adapted MERS coronavirus causes lethal lung disease in human DPP4 knockin mice. *Proc Natl Acad Sci USA* 2017, 114 (15), E3119-E3128.
15. Gao, X.; Qin, B.; Chen, P.; Zhu, K.; Hou, P.; Wojdyla, J. A.; Wang, M.; Cui, S., Crystal structure of SARS-CoV-2 papain-like protease. *Acta Pharm Sin B* 2021, 11 (1), 237-245.
16. Fu, Z.; Huang, B.; Tang, J.; Liu, S.; Liu, M.; Ye, Y.; Liu, Z.; Xiong, Y.; Zhu, W.; Cao, D.; Li, J.; Niu, X.; Zhou, H.; Zhao, Y. J.; Zhang, G.; Huang, H., The complex structure of GRL0617 and SARS-CoV-2 PLpro reveals a hot spot for antiviral drug discovery. *Nat Commun* 2021, 12 (1), 488.
17. Zhao, Y.; Du, X.; Duan, Y.; Pan, X.; Sun, Y.; You, T.; Han, L.; Jin, Z.; Shang, W.; Yu, J.; Guo, H.; Liu, Q.; Wu, Y.; Peng, C.; Wang, J.; Zhu, C.; Yang, X.; Yang, K.; Lei, Y.; Guddat, L. W.; Xu, W.; Xiao, G.; Sun, L.; Zhang, L.; Rao, Z.; Yang, H., High-throughput screening identifies established drugs as SARS-CoV-2 PLpro inhibitors. *Protein Cell* 2021.
18. Yuan, S.; Yin, X.; Meng, X.; Chan, J. F.; Ye, Z. W.; Riva, L.; Pache, L.; Chan, C. C.; Lai, P. M.; Chan, C. C.; Poon, V. K.; Lee, A. C.; Matsunaga, N.; Pu, Y.; Yuen, C. K.; Cao, J.; Liang, R.; Tang, K.; Sheng, L.; Du, Y.; Xu, W.; Lau, C. Y.; Sit, K. Y.; Au, W. K.; Wang, R.; Zhang, Y. Y.; Tang, Y. D.; Clausen, T. M.; Pihl, J.; Oh, J.; Sze, K. H.; Zhang, A. J.; Chu, H.; Kok, K. H.; Wang, D.; Cai, X. H.; Esko, J. D.; Hung, I F.; Li, R. A.; Chen, H.; Sun, H.; Jin, D. Y.; Sun, R.; Chanda, S. K.; Yuen, K. Y., Clofazimine broadly inhibits coronaviruses including SARS-CoV-2. *Nature* 2021, 593 (7859), 418-423.
19. Yuan, S.; Wang, R.; Chan, J. F.; Zhang, A. J.; Cheng, T.; Chik, K. K.; Ye, Z. W.; Wang, S.; Lee, A. C.; Jin, L.; Li, H.; Jin, D. Y.; Yuen, K. Y.; Sun, H., Metallodrug ranitidine bismuth citrate suppresses SARS-CoV-2 replication and relieves virus-associated pneumonia in Syrian hamsters. *Nature microbiology* 2020, 5 (11), 1439-1448.
20. Yuan, S.; Chu, H.; Huang, J.; Zhao, X.; Ye, Z. W.; Lai, P. M.; Wen, L.; Cai, J. P.; Mo, Y.; Cao, J.; Liang, R.; Poon, V. K.; Sze, K. H.; Zhou, J.; To, K. K.; Chen, Z.; Chen, H.; Jin, D. Y.; Chan, J. F.; Yuen, K. Y., Viruses harness YxxO motif to interact with host AP2M1 for replication: A vulnerable broad-spectrum antiviral target. *Sci Adv* 2020, 6 (35), eaba7910.
21. Berman, H. M.; Westbrook, J.; Feng, Z.; Gilliland, G.; Bhat, T. N.; Weissig, H.; Shindyalov, I. N.; Bourne, P. E., The Protein Data Bank. *Nucleic Acids Res* 2000, 28 (1), 235-42.
22. Olsson, M. H. M.; Sondergaard, C. R.; Rostkowski, M.; Jensen, J. H., PROPKA3: Consistent Treatment of Internal and Surface Residues in Empirical pKa Predictions. *Journal of Chemical Theory and Computation* 2011, 7 (2), 525-537.
23. O'Boyle, N. M.; Banck, M.; James, C. A.; Morley, C.; Vandermeersch, T.; Hutchison, G. R., Open Babel: An open chemical toolbox. *Journal of Cheminformatics* 2011, 3 (1), 33.

24. Trott, O.; Olson, A. J., AutoDock Vina: improving the speed and accuracy of docking with a new scoring function, efficient optimization, and multithreading. *Journal of computational chemistry* 2010, 31 (2), 455-461.
25. Yuan, S.; Chu, H.; Chan, J. F.; Ye, Z. W.; Wen, L.; Yan, B.; Lai, P. M.; Tee, K. M.; Huang, J.; Chen, D.; Li, C.; Zhao, X.; Yang, D.; Chiu, M. C.; Yip, C.; Poon, V. K.; Chan, C. C.; Sze, K. H.; Zhou, J.; Chan, I. H.; Kok, K. H.; To, K. K.; Kao, R. Y.; Lau, J. Y.; Jin, D. Y.; Perlman, S.; Yuen, K. Y., SREBP-dependent lipidomic reprogramming as a broad-spectrum antiviral target. *Nature communications* 2019, 10 (1), 120.
26. Chu, H.; Shuai, H.; Hou, Y.; Zhang, X.; Wen, L.; Huang, X.; Hu, B.; Yang, D.; Wang, Y.; Yoon, C.; Wong, B. H.; Li, C.; Zhao, X.; Poon, V. K.; Cai, J. P.; Wong, K. K.; Yeung, M. L.; Zhou, J.; Au-Yeung, R. K.; Yuan, S.; Jin, D. Y.; Kok, K. H.; Perlman, S.; Chan, J. F.; Yuen, K. Y., Targeting highly pathogenic coronavirus-induced apoptosis reduces viral pathogenesis and disease severity. *Sci Adv* 2021, 7 (25).

---

We claim:

1. A method for prophylactic or responsive treatment of a human coronavirus infection or a symptom thereof in a human subject, said method comprising administering an effective amount of a papain-like protease (PLpro) inhibitor to the human subject, wherein the PLpro inhibitor is F0213, according to formula (I); F0326, according to formula (II); and/or F0393, according to formula (III), or a pharmaceutically acceptable salt, derivative, or prodrug of any thereof:

formula (I)

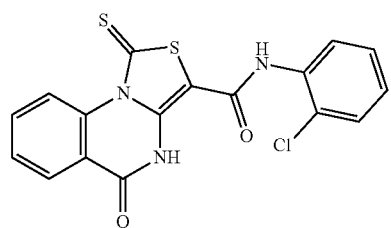

formula (II)

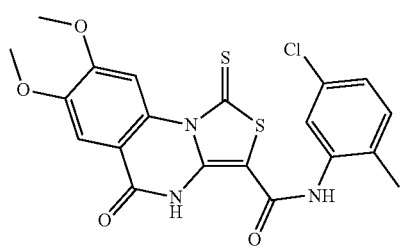

formula (III)

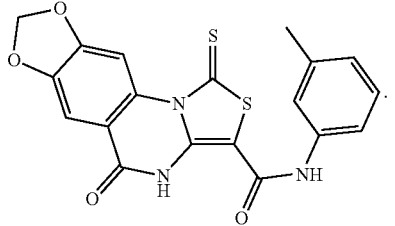

2. The method of claim 1, wherein the coronavirus is SARS-CoV-2.

3. The method of claim 1, wherein the coronavirus is SARS-CoV.

4. The method of claim 1, wherein the coronavirus is MERS-CoV.

5. The method of claim 1, wherein the human coronavirus is a common human coronavirus selected from 229E, NL63, OC43, and HKU1.

6. The method of claim 1, wherein the human subject has the coronavirus infection at the time of said administering.

7. The method of claim 1, wherein the human subject has previously had the coronavirus infection at the time of said administering.

8. The method of claim 7, further comprising, prior to said administering, identifying the subject as having the coronavirus infection, wherein said identifying comprises assaying a biological sample obtained from the subject for the presence of coronavirus nucleic acid or coronavirus protein.

9. The method of claim 1, wherein the human subject does not have the coronavirus infection at the time of said administering, and the PLpro inhibitor is administered as prophylaxis.

10. The method of claim 1, wherein the PLpro inhibitor is administered orally, intravascularly, nasally, rectally, parenterally, subcutaneously, or intramuscularly.

11. The method of claim 10, wherein the PLpro inhibitor is administered orally or intravenously.

12. The method of claim 1, wherein the PLpro inhibitor inhibits cleavage of Interferon-stimulated gene 15 (ISG15) from substrates or inhibits cleavage of ubiquitin chains.

13. A composition of matter, comprising a combination of at least two compounds selected from F0213, according to formula (I); F0326, according to formula (II); and/or F0393, according to formula (III), or a pharmaceutically acceptable salt, derivative, or prodrug of any thereof:

formula (I)

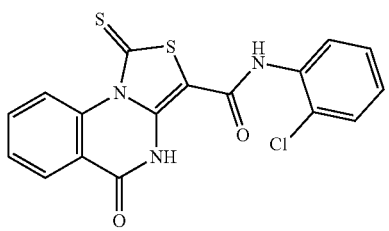

formula (II)

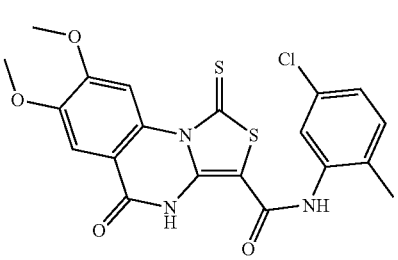

formula (III)

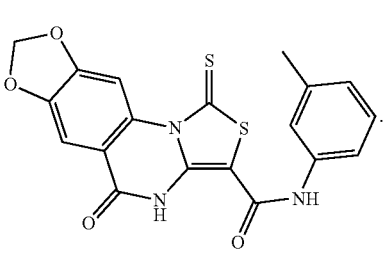

14. The composition of matter of claim 13, wherein the composition further comprises a pharmaceutically acceptable carrier.

* * * * *

SEQUENCE LISTING

```
Sequence total quantity: 6
SEQ ID NO: 1            moltype = DNA  length = 22
FEATURE                 Location/Qualifiers
source                  1..22
                        mol_type = genomic DNA
                        organism = human coronavirus
SEQUENCE: 1
ctacagatag aaaagttgct tt                                          22

SEQ ID NO: 2            moltype = DNA  length = 21
FEATURE                 Location/Qualifiers
source                  1..21
                        mol_type = genomic DNA
                        organism = human coronavirus
SEQUENCE: 2
ggtcgtttag ttgagaaaag t                                           21

SEQ ID NO: 3            moltype = DNA  length = 15
FEATURE                 Location/Qualifiers
source                  1..15
                        mol_type = genomic DNA
                        organism = human coronavirus
SEQUENCE: 3
aaacgtgcgt gcatc                                                  15

SEQ ID NO: 4            moltype = DNA  length = 24
FEATURE                 Location/Qualifiers
source                  1..24
                        mol_type = genomic DNA
                        organism = human coronavirus
SEQUENCE: 4
agattacaaa aagatctaac aaga                                        24

SEQ ID NO: 5            moltype = DNA  length = 26
FEATURE                 Location/Qualifiers
source                  1..26
                        mol_type = genomic DNA
                        organism = human coronavirus
SEQUENCE: 5
ggagatagag aattttctta tttaga                                      26

SEQ ID NO: 6            moltype = DNA  length = 20
FEATURE                 Location/Qualifiers
source                  1..20
                        mol_type = genomic DNA
                        organism = human coronavirus
SEQUENCE: 6
ggtttcgttt agttgagaag                                             20
```